US011857585B2

(12) United States Patent
Hwang et al.

(10) Patent No.: US 11,857,585 B2
(45) Date of Patent: Jan. 2, 2024

(54) ONCOLYTIC VIRUS IMPROVED IN SAFETY AND ANTICANCER EFFECT

(71) Applicant: BIONOXX INC., Seongnam-si (KR)

(72) Inventors: Taeho Hwang, Yangsan-si (KR); Mong Cho, Yangsan-si (KR)

(73) Assignee: BIONOXX INC., Seongnam-si (KR)

( * ) Notice: Subject to any disclaimer, the term of this patent is extended or adjusted under 35 U.S.C. 154(b) by 664 days.

(21) Appl. No.: 16/957,511

(22) PCT Filed: Dec. 28, 2018

(86) PCT No.: PCT/KR2018/016874
§ 371 (c)(1),
(2) Date: Jun. 24, 2020

(87) PCT Pub. No.: WO2019/132596
PCT Pub. Date: Jul. 4, 2019

(65) Prior Publication Data
US 2021/0060103 A1    Mar. 4, 2021

Related U.S. Application Data

(60) Provisional application No. 62/611,174, filed on Dec. 28, 2017.

(30) Foreign Application Priority Data

Sep. 7, 2018   (KR) .......................... 10-2018-0106841

(51) Int. Cl.
*A61K 35/768*     (2015.01)
*C12N 15/86*     (2006.01)
(Continued)

(52) U.S. Cl.
CPC .......... *A61K 35/768* (2013.01); *A61K 9/0019* (2013.01); *A61K 31/708* (2013.01); *C12N 15/86* (2013.01); *C12N 2710/24111* (2013.01)

(58) Field of Classification Search
None
See application file for complete search history.

(56) References Cited

U.S. PATENT DOCUMENTS

| 6,004,803 A | 12/1999 | Klatzmann et al. |
| 2009/0130069 A1 | 5/2009 | Radrizzani et al. |

(Continued)

FOREIGN PATENT DOCUMENTS

| JP | 10-503641 A | 4/1998 |
| JP | 10-506007 A | 6/1998 |

(Continued)

OTHER PUBLICATIONS

Mizuno et al. (Japanese Journal of Cancer Research. 1998; 89: 76-80).*

(Continued)

*Primary Examiner* — Shanon A. Foley
(74) *Attorney, Agent, or Firm* — Sughrue Mion, PLLC

(57) ABSTRACT

A recombinant oncolytic virus with improved safety and anticancer effect and a use thereof are disclosed. The recombinant oncolytic virus is obtained by inserting an HSV-TK fragment-encoding gene into a TK gene region to delete TK of Vaccinia virus. The oncolytic virus expresses an HSV-TK fragment to phosphorylate GCV so that cancer cells infected with the oncolytic virus and their neighboring cancer cells can be killed. GCV is also involved in the suppression of viral proliferation and thus can control side effects caused by a virus even upon the administration of a high dose of the virus.

16 Claims, 28 Drawing Sheets

Specification includes a Sequence Listing.

(51) Int. Cl.
*A61K 9/00* (2006.01)
*A61K 31/708* (2006.01)

(56) References Cited

U.S. PATENT DOCUMENTS

2014/0369979 A1   12/2014  Sung et al.
2021/0060103 A1*   3/2021  Hwang ................ A61K 31/708

FOREIGN PATENT DOCUMENTS

| KR | 2000-0056226 A | 9/2000 |
| KR | 10-2013-0089214 A | 8/2013 |
| WO | 95/30007 A1 | 11/1995 |
| WO | 2016/170176 A1 | 10/2016 |

OTHER PUBLICATIONS

Fetzer et al. (Virus Genes. 1993; 7 (2): 205-209).*
SEQ 7 published app db with SEQ 3 and 7 of 17595220 2019.*
SEQ 8 published app db with SEQ 11 of 17595220 2019.*
Swain and Galloway (Journal of Virology. 1983. 46 (3): 1045-1050).*
Saijo et al. (Journal of Medical Virology. 2002; 66: 388-393).*
UniProt database accession No. Q9IYZ8_HHV1 shares 99% identity with instant SEQ ID No. 7—2001.*
UniProt database accession No. G0YGB3_HHV1 shares 99% identity with instant SEQ ID No. 4—2011.*
UniProt database accession No. Q9ENS0_HHV1 shares 99% identity with instant SEQ ID No. 3—2001.*
Islam et al. (Biomedicines. 2020; 8 (426)).*
Kokoris et al. (Protein Science. 2002; 11: 2267-2272).*
Birringer et al. (Protein Expression and Purification. 2006; 47: 506-515).*
Robert L. Martuza et al., "Experimental Therapy of Human Glioma by Means of a Genetically Engineered Virus Mutant", Science, May 10, 1991, pp. 854-856, vol. 252.
Tae-Ho Hwang et al., "A Mechanistic Proof-of-concept Clinical Trial with JX-594, a Targeted Multi-mechanistic Oncolytic Poxvirus, in Patients with Metastatic Melanoma", Molecular Therapy, Oct. 2011, pp. 1913-1922, vol. 19, No. 10.
Howard L. Kaufman et al., "Oncolytic viruses: a new class of immunotherapy drugs", Nature Reviews, Sep. 2015, pp. 642-662, vol. 14.
Fadlo R. Khuri et al., "A controlled trial of intratumoral ONYX-015, a selectively replicating adenovirus, in combination with cisplatin and 5-fluorouracil in patients with recurrent head and neck cancer", Nature America Inc., Aug. 2000, pp. 879-885, vol. 6, No. 8.
Byeong-Ho Park et al., "Use of a targeted oncolytic poxvirus, JX-594, in patients with refractory primary or metastatic liver cancer: a phase I trial", The Lancet, Jun. 2008, pp. 533-542, vol. 9.
Jeong Heo et al., "Randomized dose-finding clinical trial of oncolytic immunotherapeutic vaccinia JX-594 in liver cancer", NIH Public Access, Nat. Med., Mar. 2013, pp. 329-336, vol. 19, No. 3.
Oliver Wildner et al., "Synergy between the Herpes Simplex Virus tk/Ganciclovir Prodrug Suicide System and the Topoisomerase I Inhibitor Topotecan", Human Gene Therapy, Nov. 1, 1999, pp. 2679-2687, vol. 10, No. 16.
Es Lambright et al., "Inclusion of the herpes simplex thymidine kinase gene in a replicating adenovirus does not augment antitumor efficacy", Research Article, Gene Therapy, 2011, pp. 946-953, vol. 8.
John C. Morris et al., "Therapy of Head and Neck Squamous Cell Carcinoma with an Oncolytic Adenovirus Expressing HSV-tk", Molecular Therapy, Jan. 2000, pp. 56-62, vol. 1, No. 1.
Masayuki Saijo et al., "Importance of C-Terminus of Herpes Simplex Virus Type 1 Thymidine Kinase for Maintaining Thymidine Kinase and Acyclovir-Phosphorylation Activities", Journal of Medical Virology, 2002, pp. 388-393, vol. 66.
Marco Redaelli et al., "Herpes simplex virus type 1 thymidine kinase-armed bovine herpesvirus type 4-based vector displays enhanced oncolytic properties in immunocompetent orthotopic syngenic mouse and rat glioma models", Neuro-Oncology, Mar. 2012, pp. 288-301, vol. 14, No. 3.
NCBI, GenBank Accession No. P06478.1, "RecName: Full= Thymidine Kinase", Oct. 14, 2015, 4 pages.
International Search Report for PCT/KR2018/016874 dated Apr. 8, 2019 [PCT/ISA/210].
NCBI, GenBank Accession No. P06478.1, "RecName: Full= Thymidine Kinase", Sep. 27, 2017 (2 pages total) Accessed via the Internet: https://www.ncbi.nlm.nih.gov/protein/125434?sat=46 &satkey=147426271, last visited on Jan. 4, 2023.

* cited by examiner

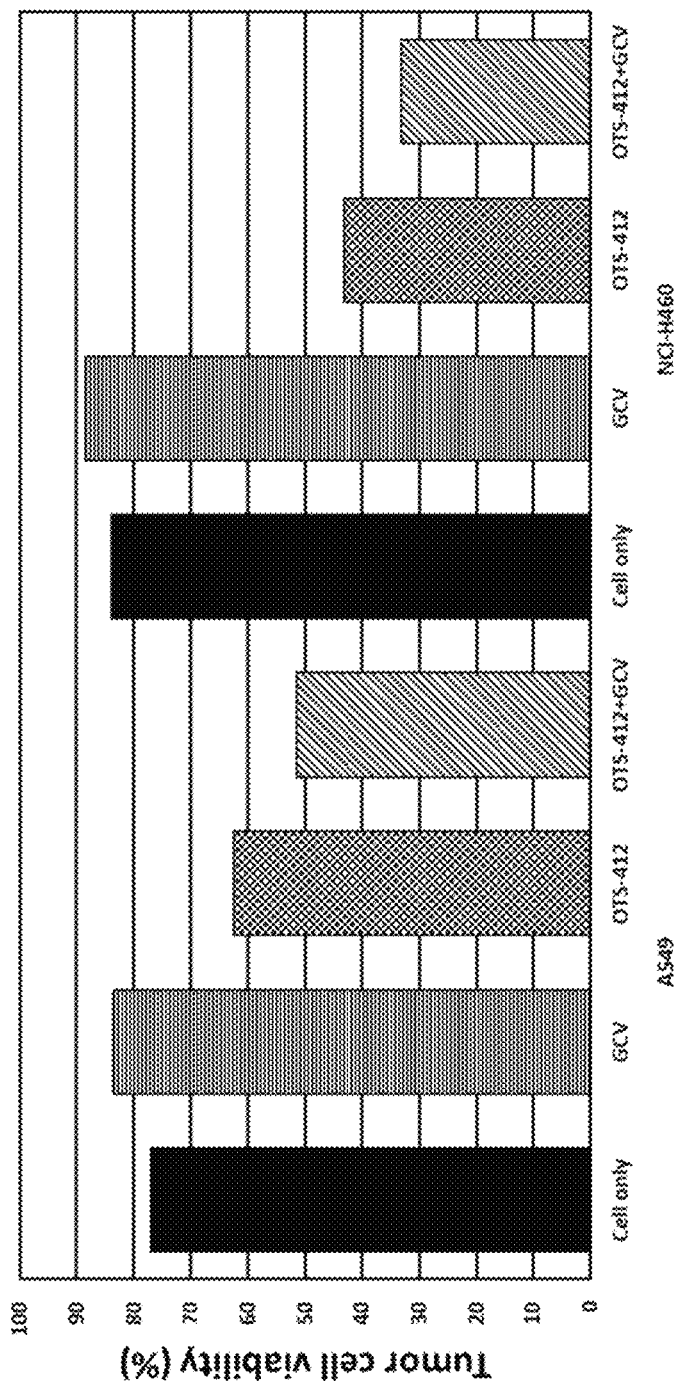
[Fig. 11]

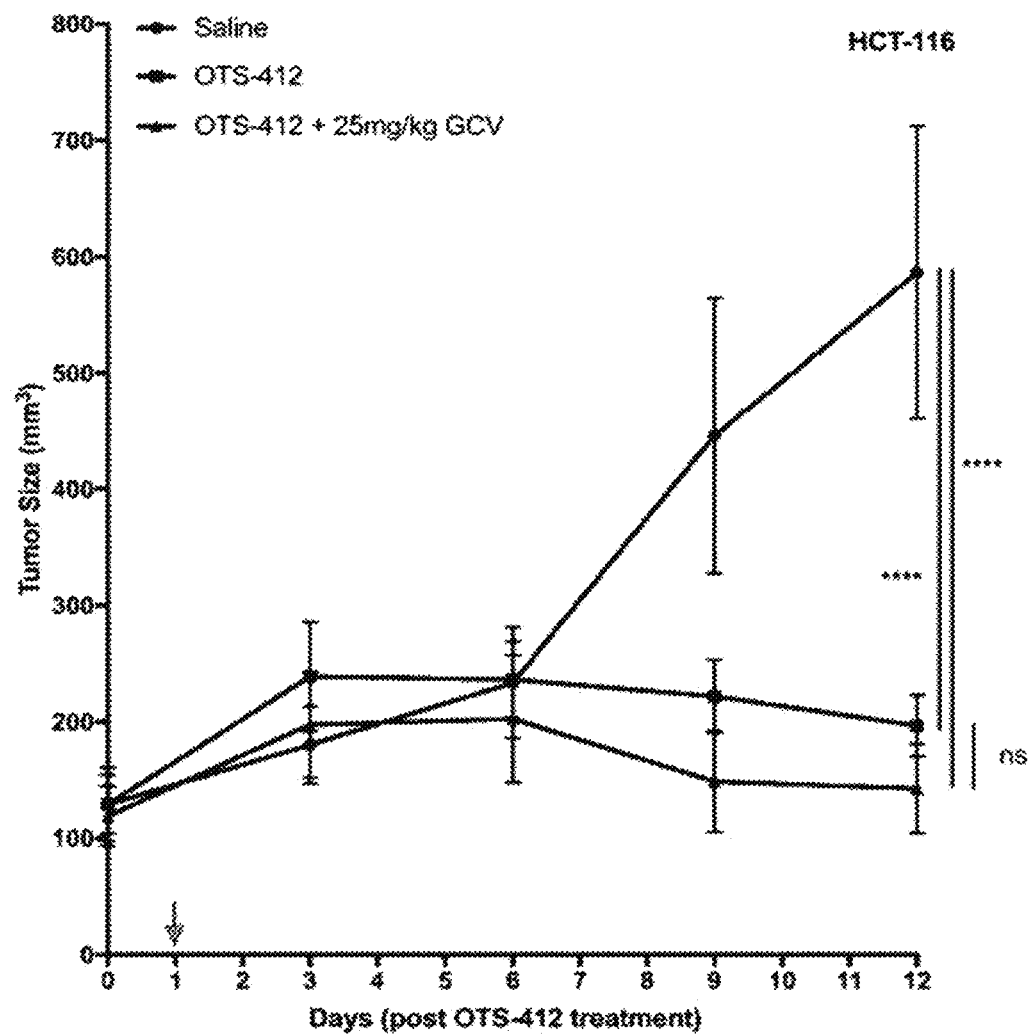

[Fig. 13]
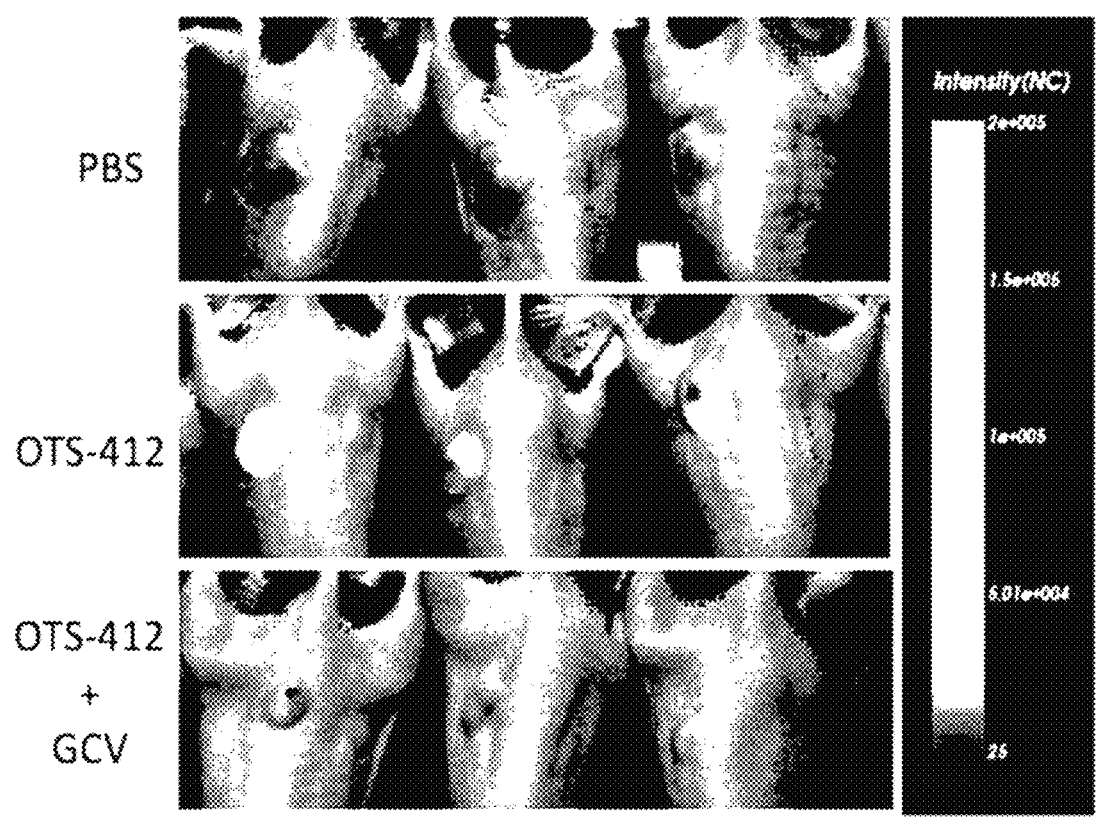

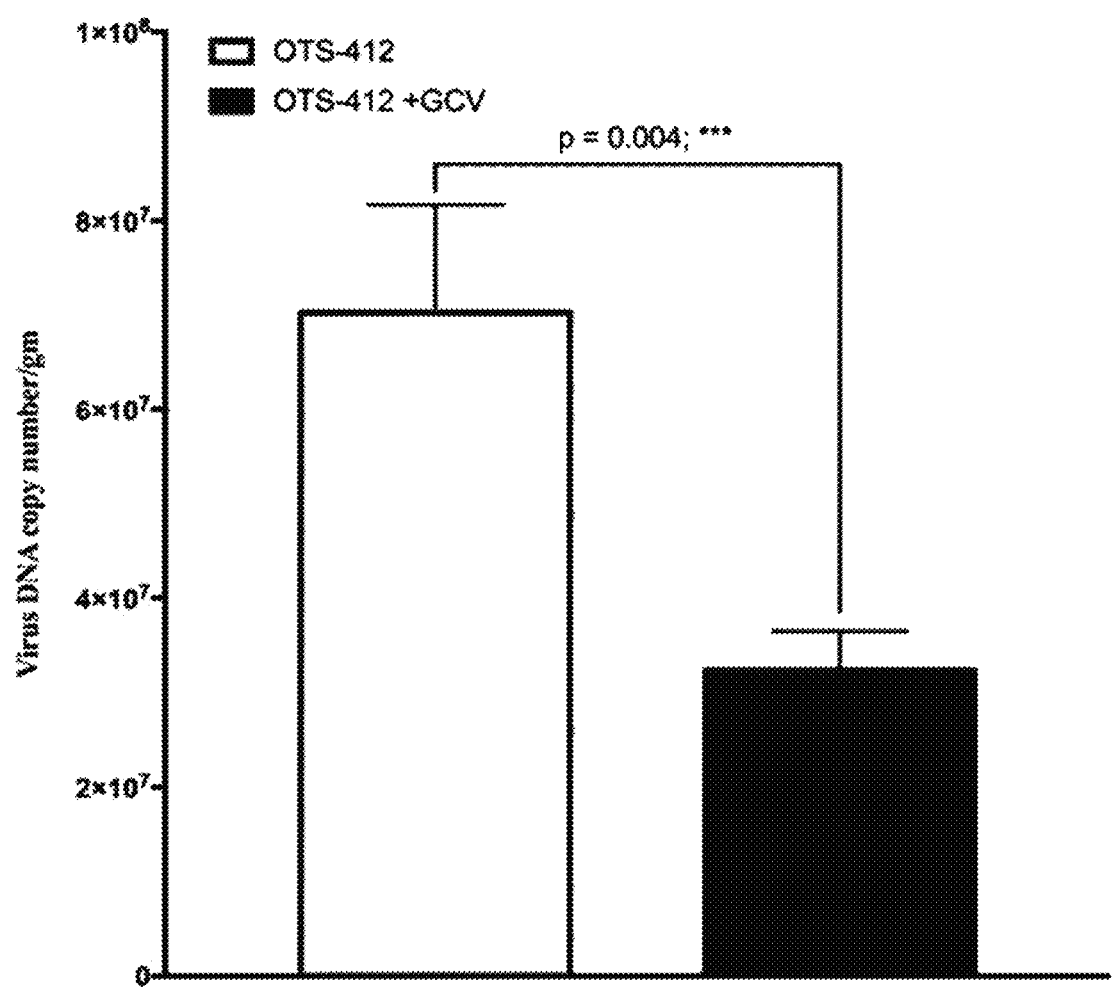
[Fig. 14]

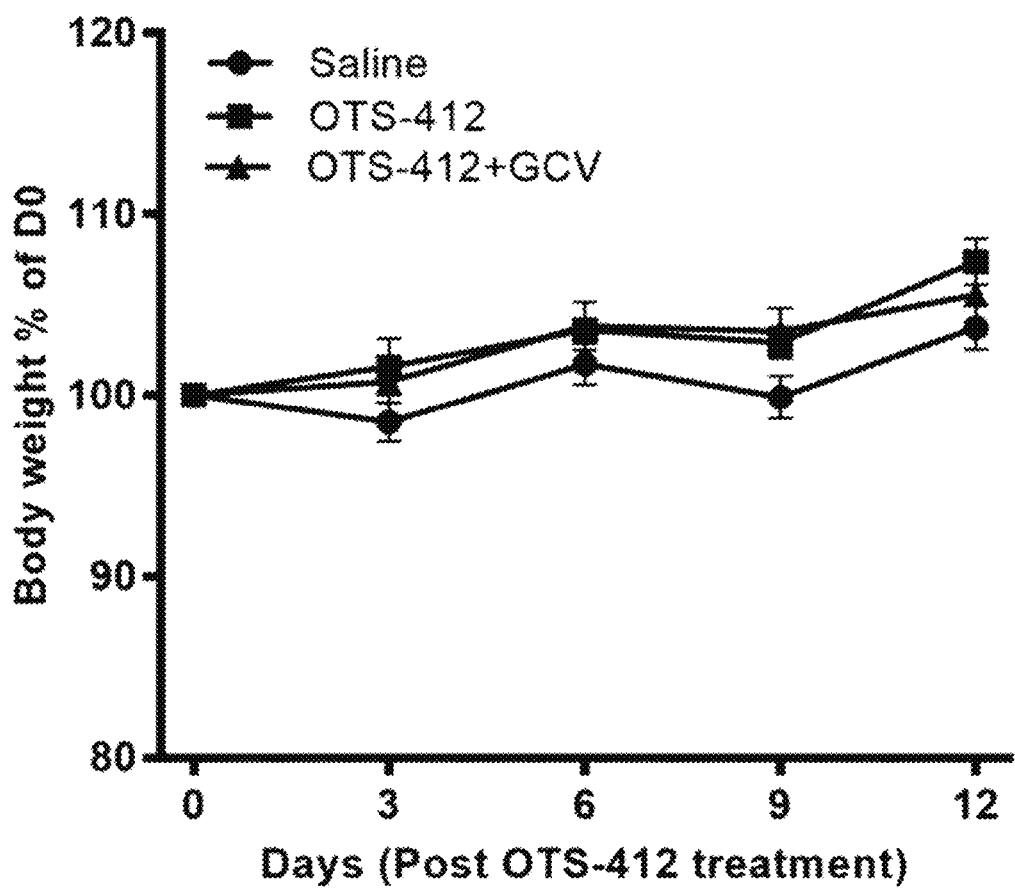
[Fig. 15]

[Fig. 16]
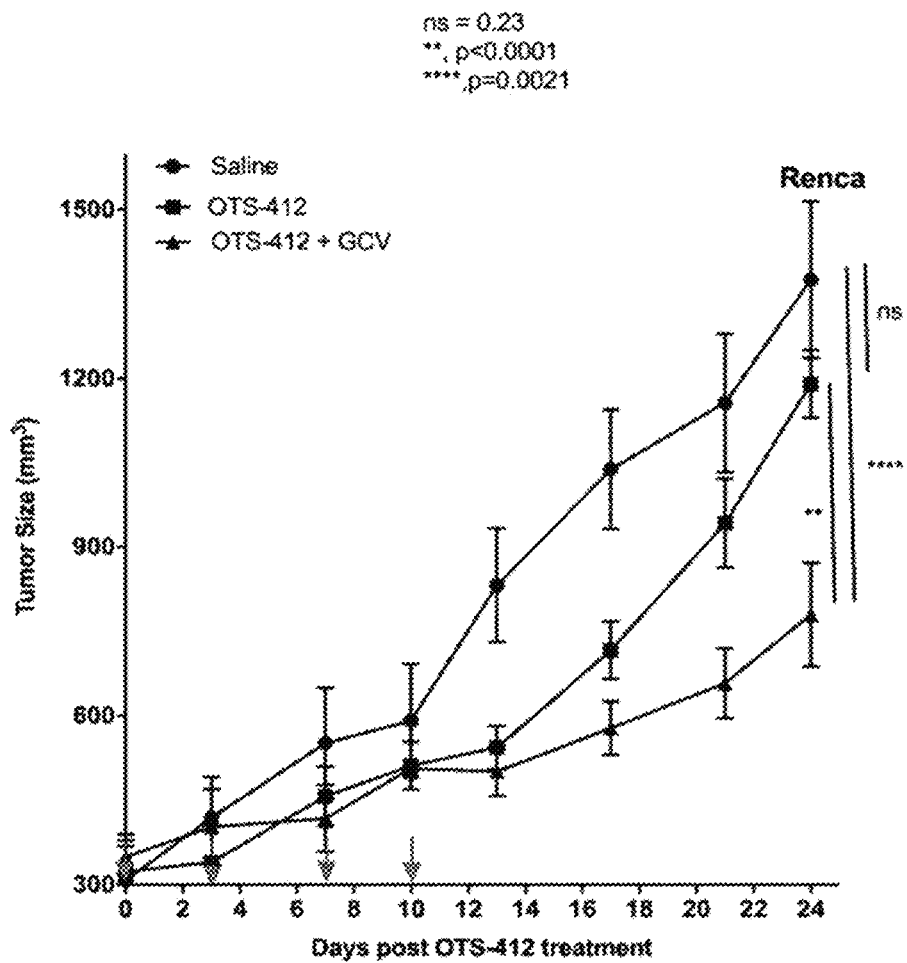

[Fig. 17]
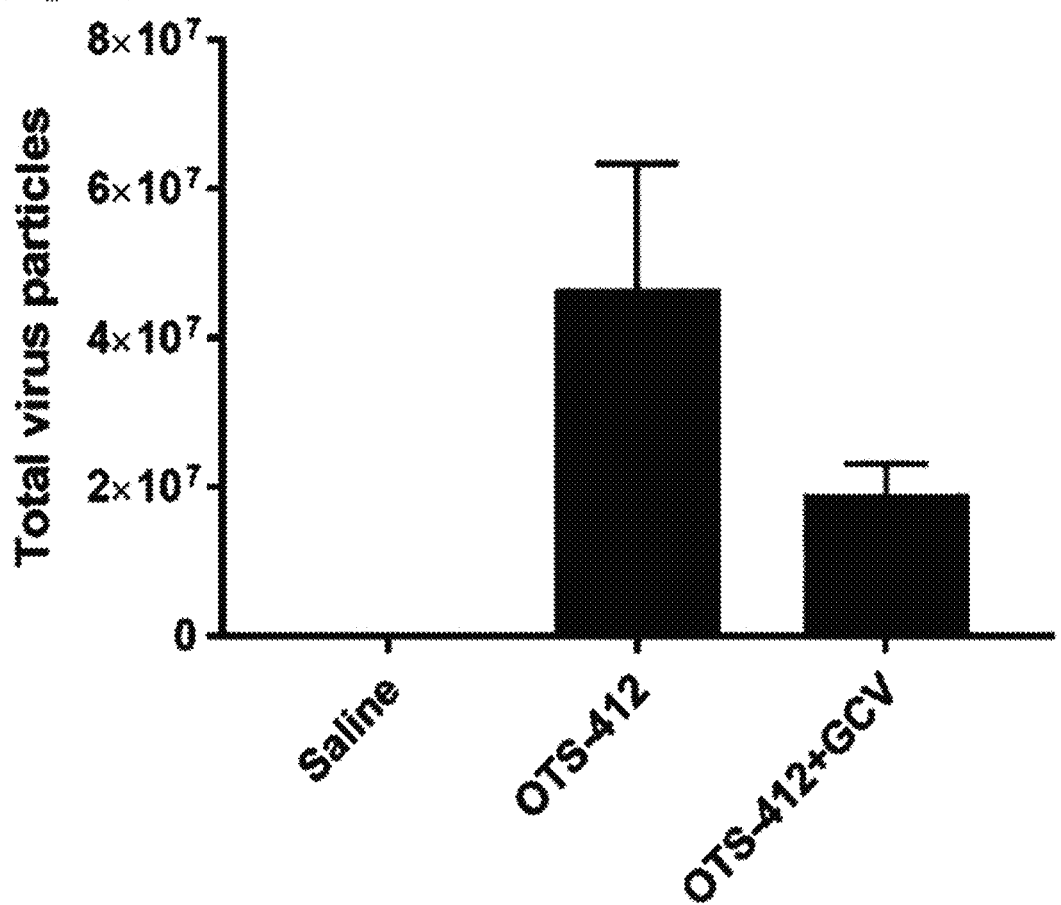

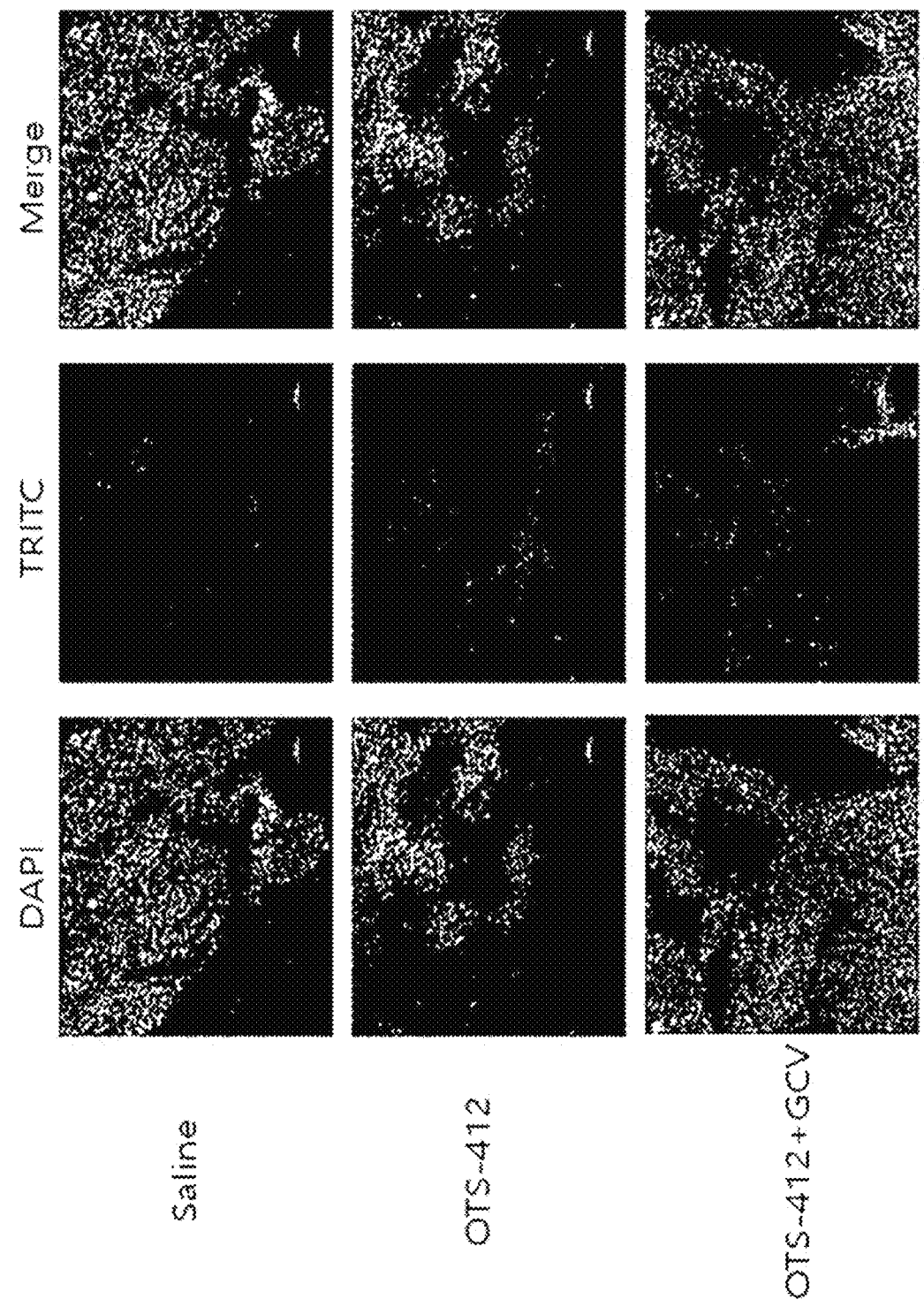
[Fig. 18]

[Fig. 19]
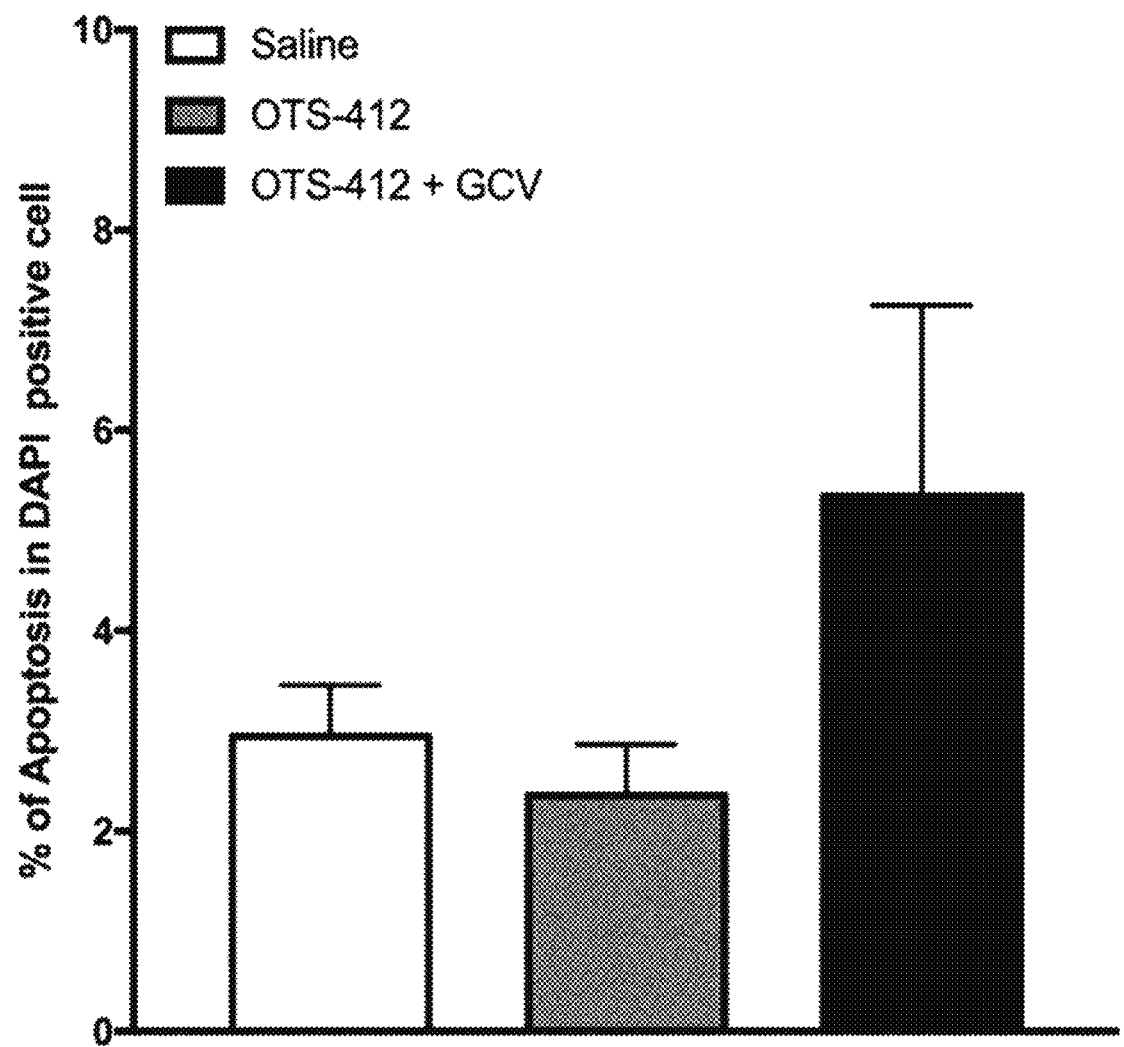

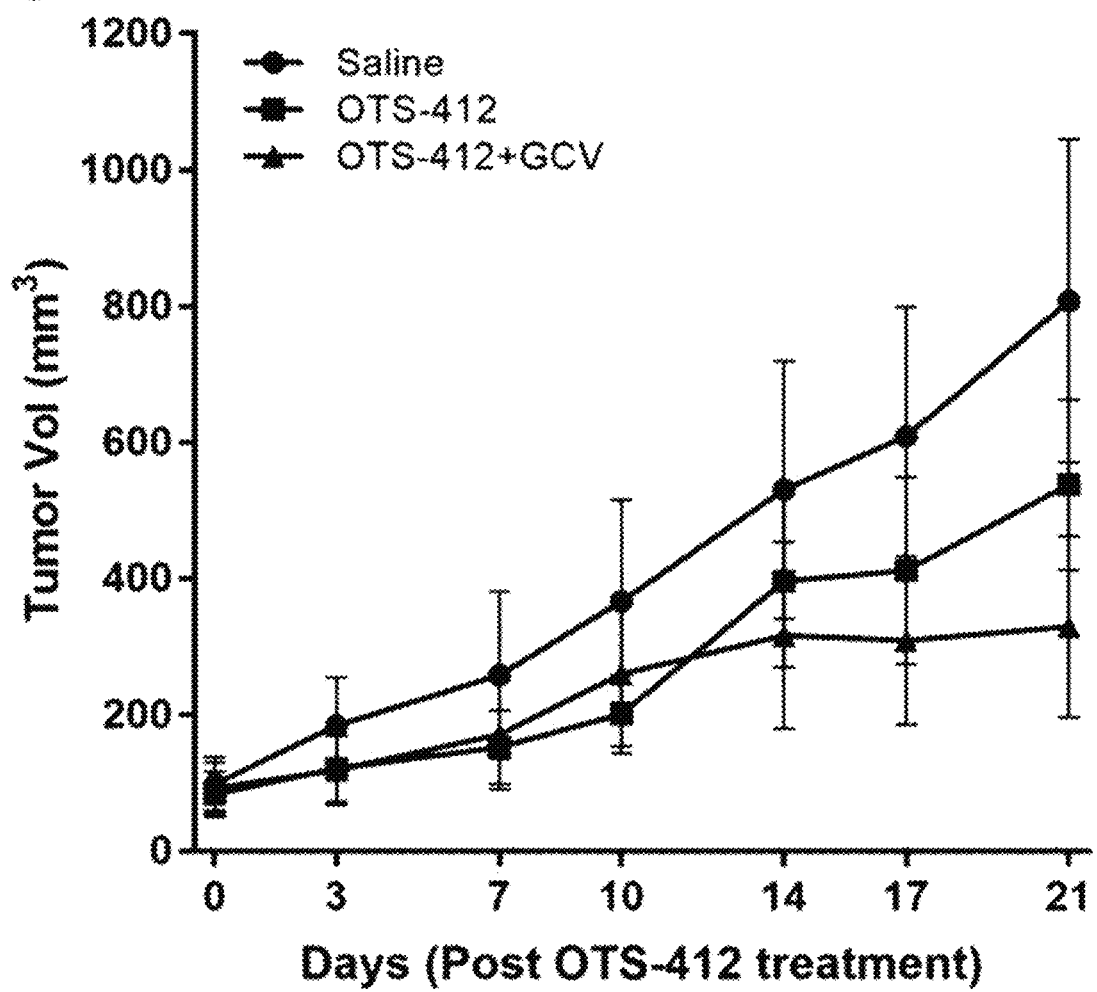
[Fig. 20]

[Fig. 21]
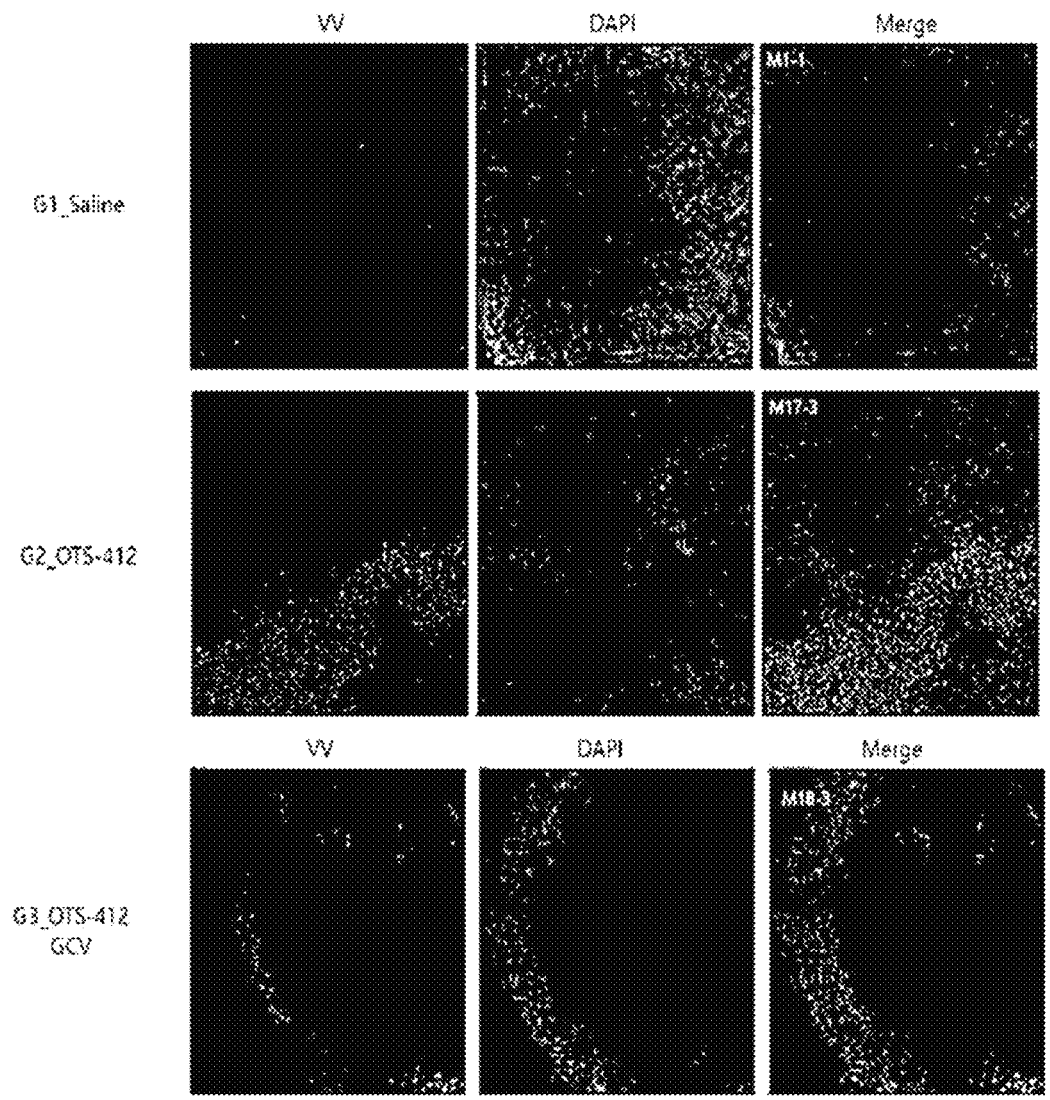
Anti-vaccinia virus : green
DAPI(nucleus staining) : blue

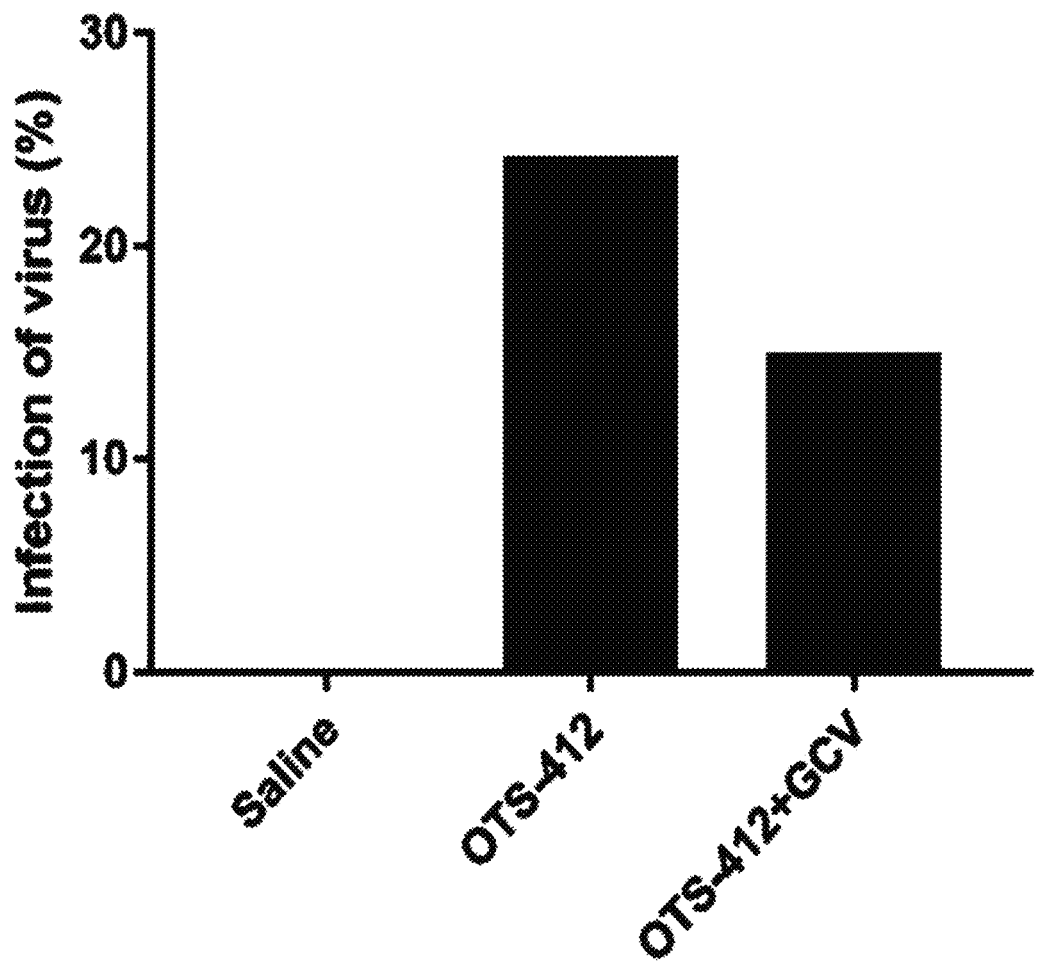
[Fig. 22]

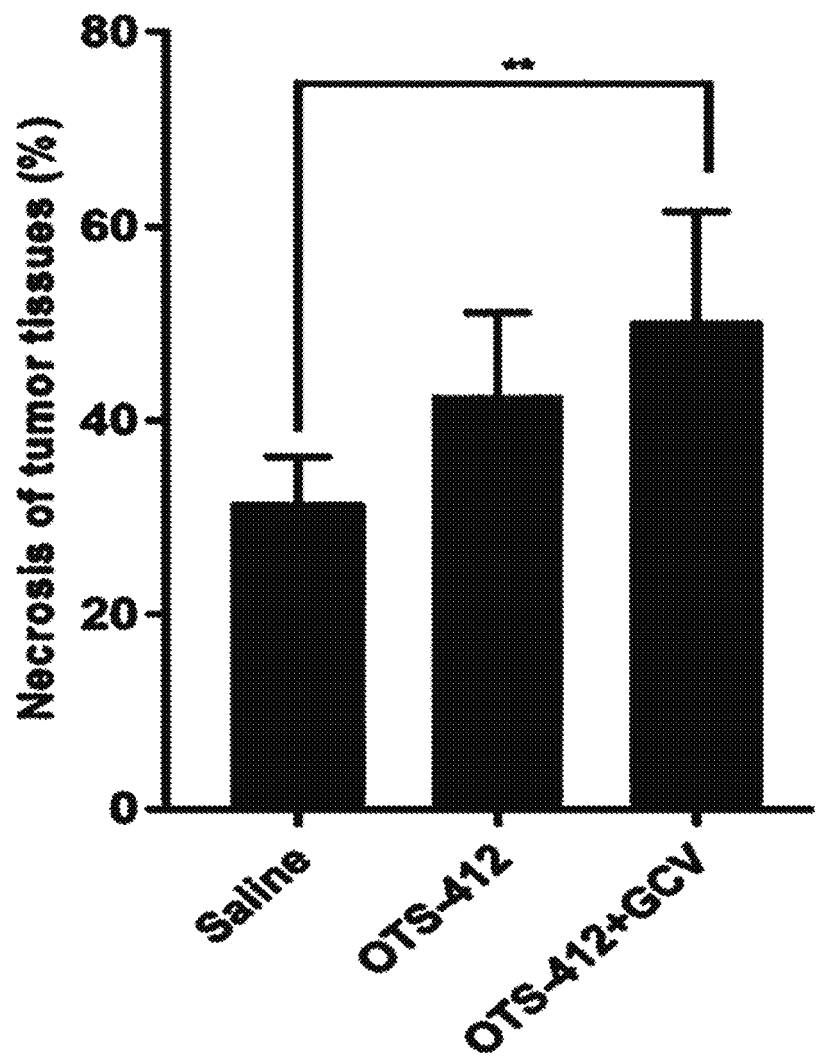
[Fig. 23]

[Fig. 24]
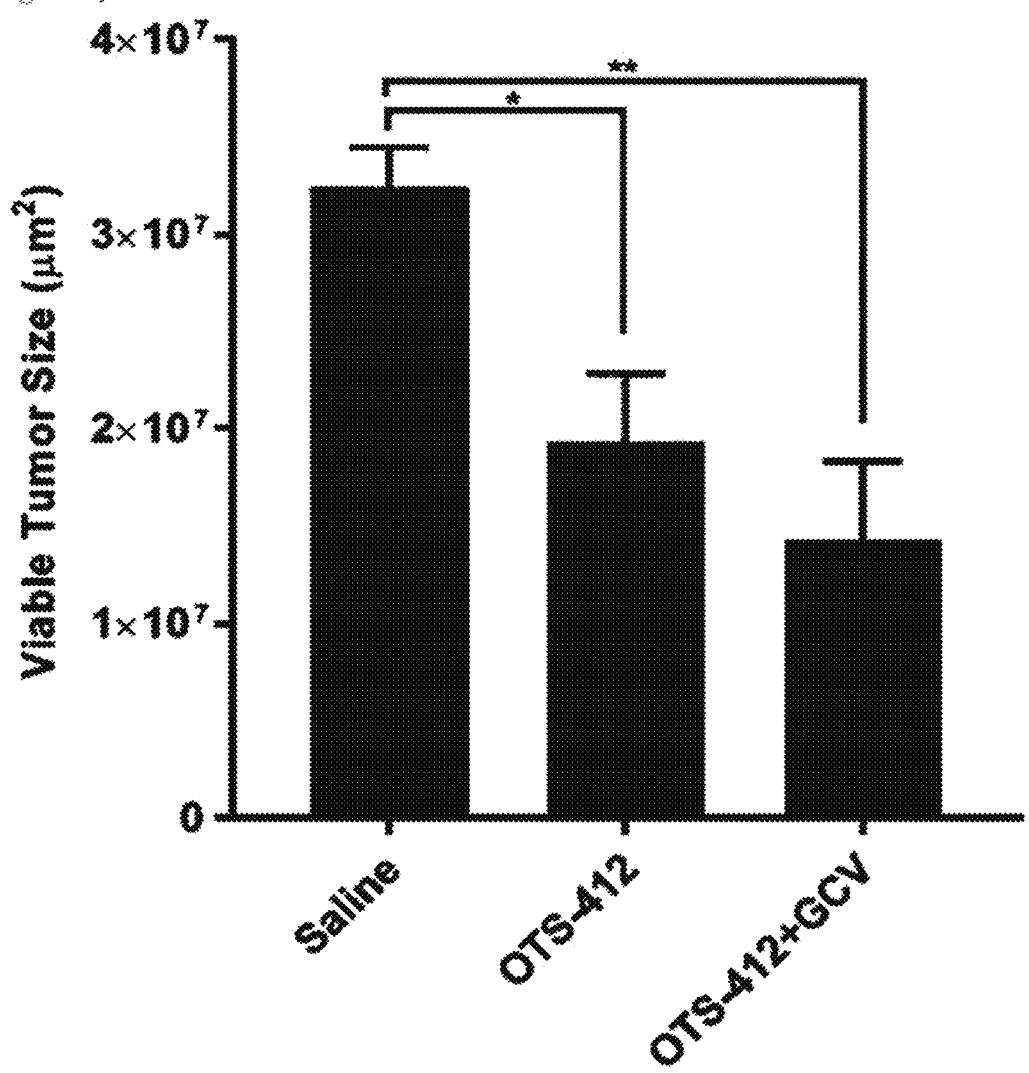

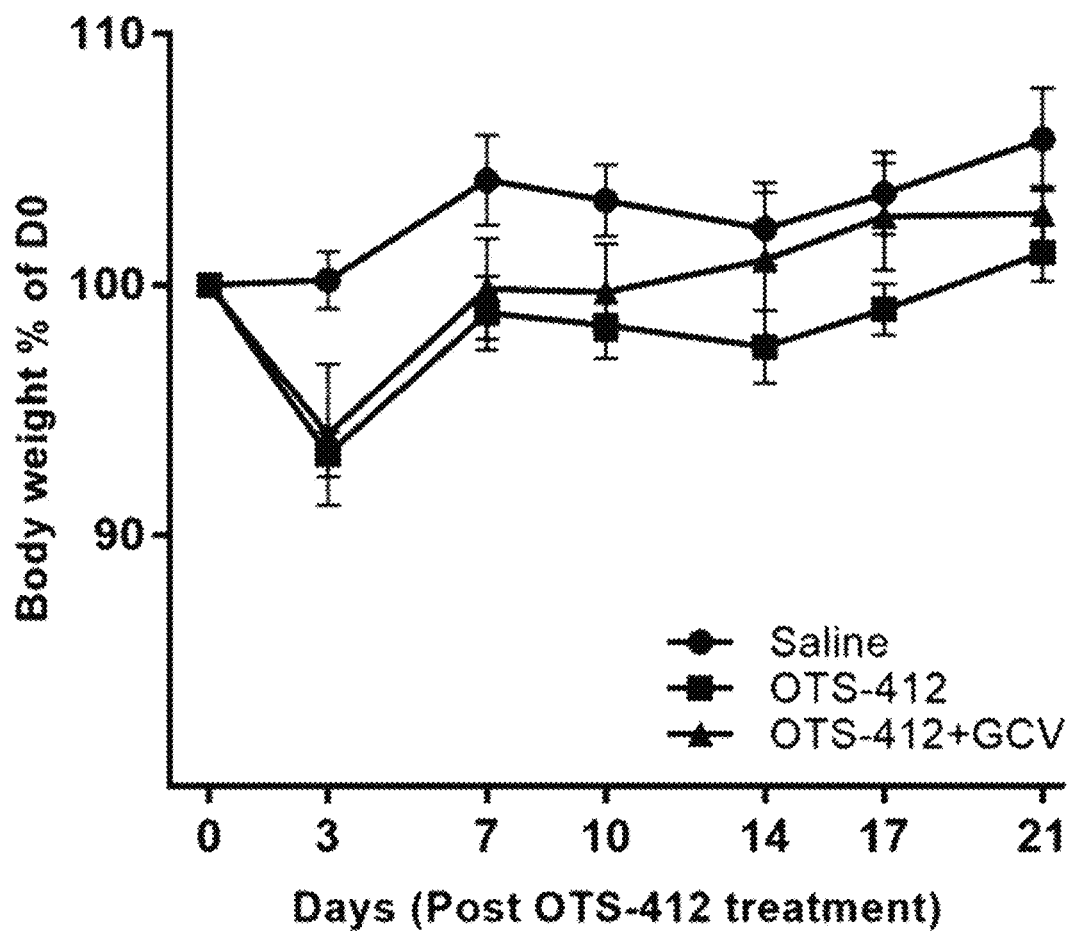
[Fig. 25]

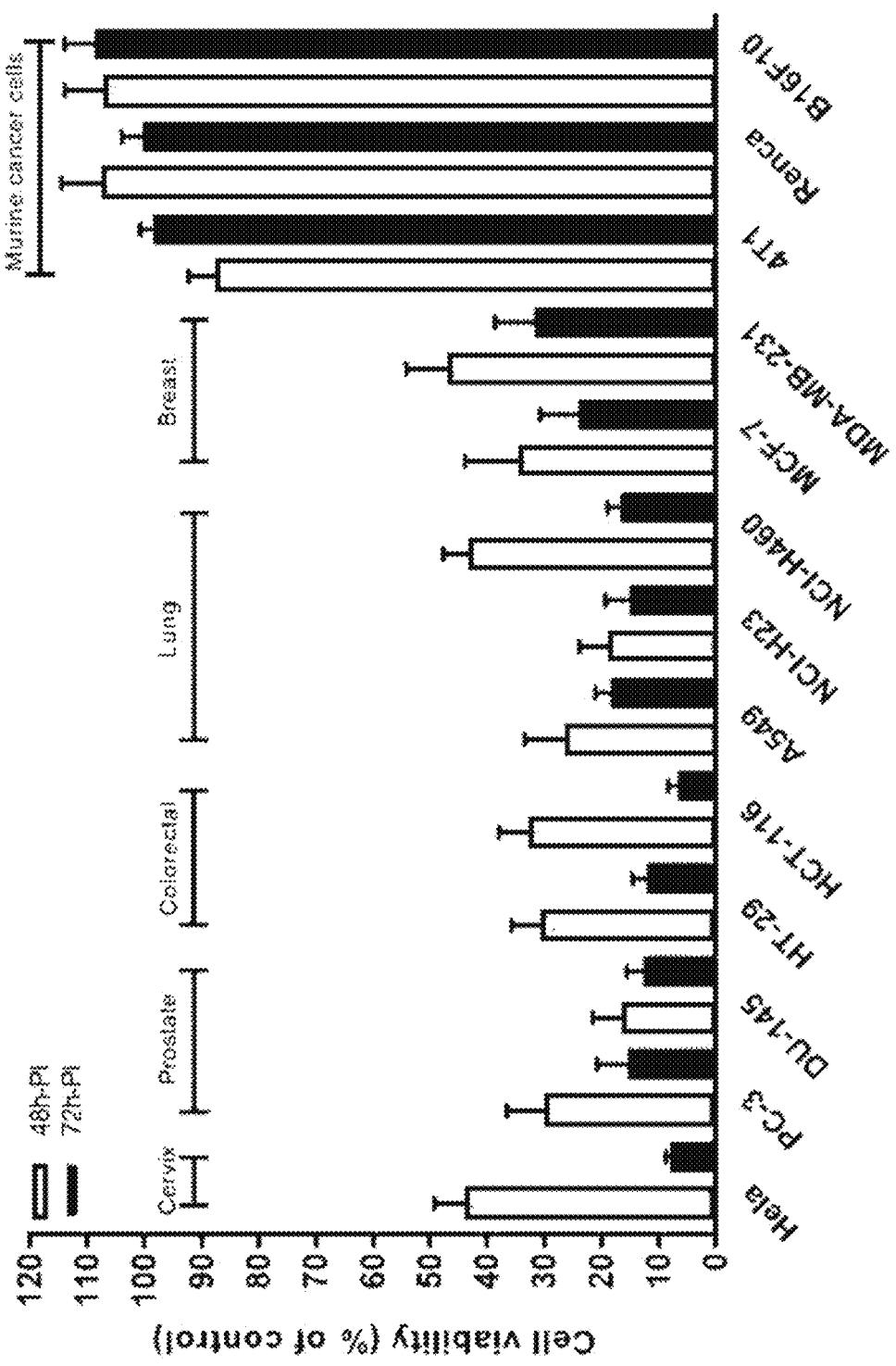
[Fig. 26]

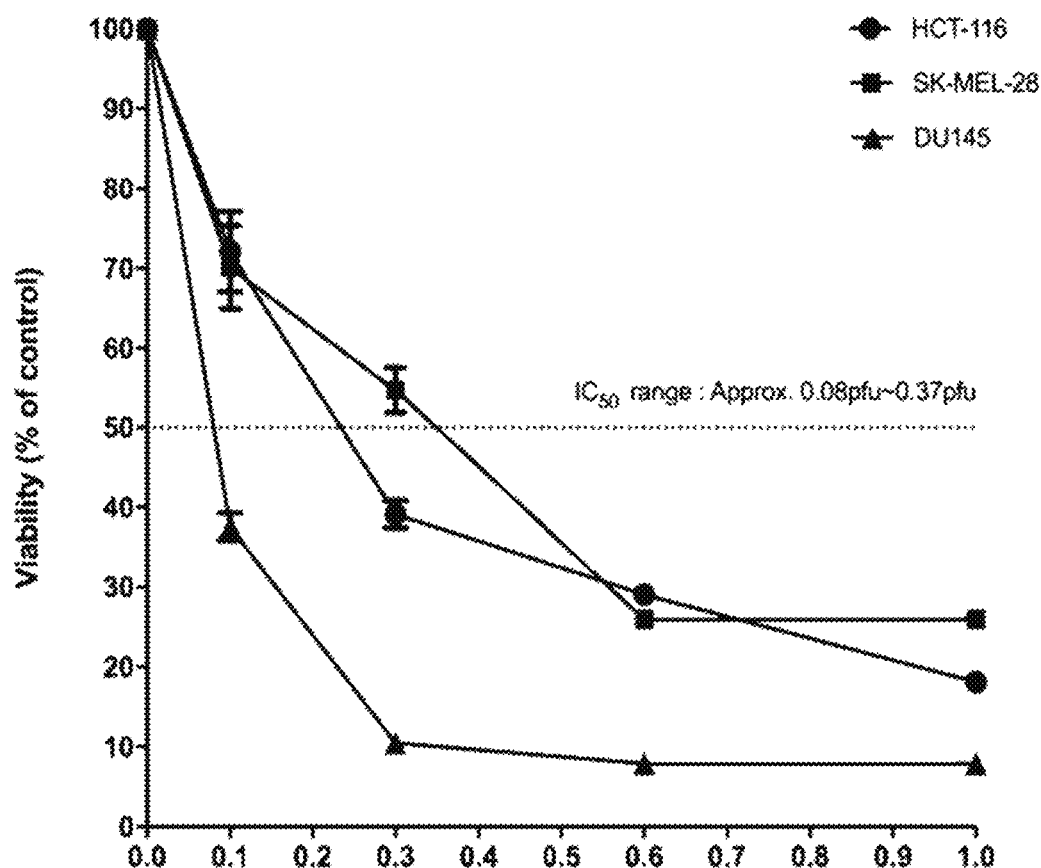
[Fig. 27]

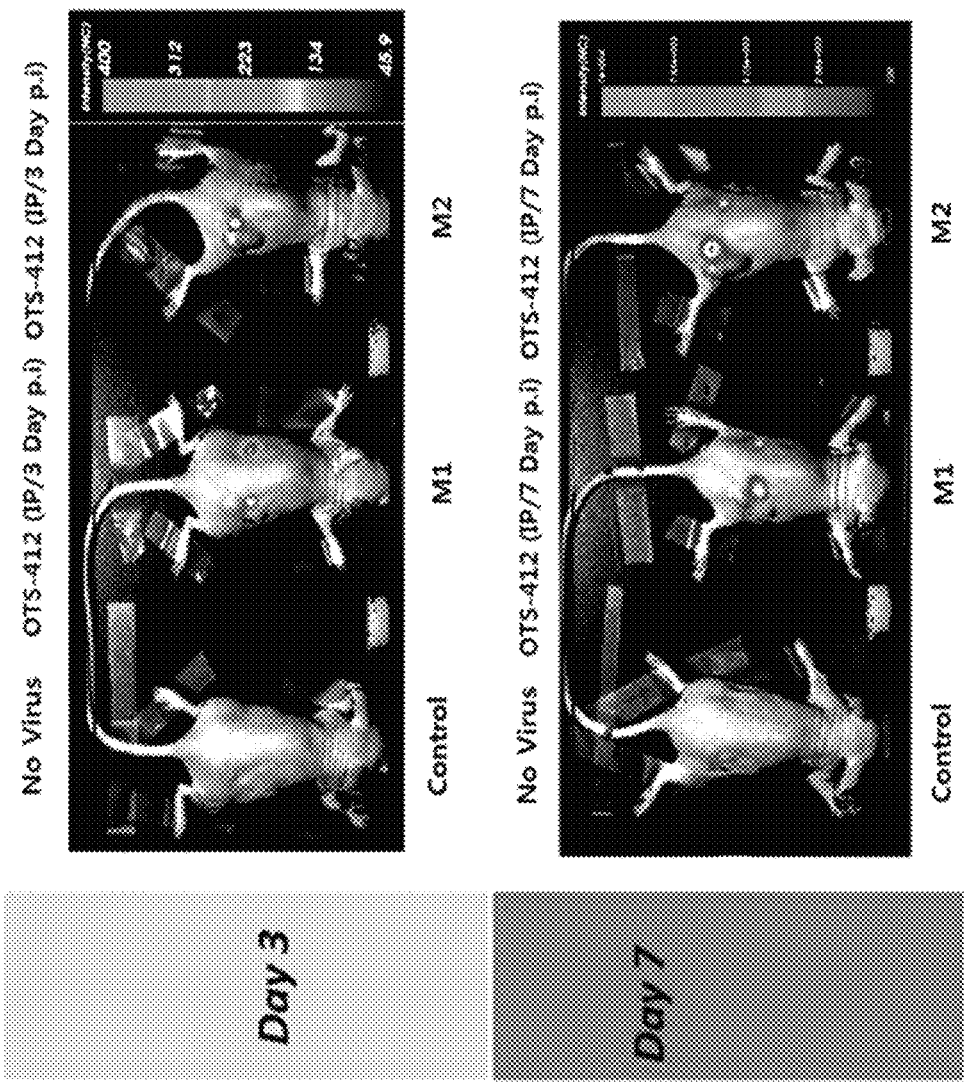
[Fig. 28]

SEQUENCE LISTING

<160> NUMBER OF SEQ ID NOS: 11

<210> SEQ ID NO 1
<211> LENGTH: 376
<212> TYPE: PRT
<213> ORGANISM: Artificial Sequence
<220> FEATURE:
<223> OTHER INFORMATION: 1-376 aa fragment of HSV1-TK (OTS-410)

<400> SEQUENCE: 1

```
Met Ala Ser Tyr Pro Cys His Gln His Ala Ser Ala Phe Asp Gln Ala
1               5                   10                  15

Ala Arg Ser Arg Gly His Ser Asn Arg Arg Thr Ala Leu Arg Pro Arg
            20                  25                  30

Arg Gln Gln Glu Ala Thr Glu Val Arg Leu Glu Gln Lys Met Pro Thr
        35                  40                  45

Leu Leu Arg Val Tyr Ile Asp Gly Pro His Gly Met Gly Lys Thr Thr
    50                  55                  60

Thr Thr Gln Leu Leu Val Ala Leu Gly Ser Arg Asp Asp Ile Val Tyr
65                  70                  75                  80

Val Pro Glu Pro Met Thr Tyr Trp Gln Val Leu Gly Ala Ser Glu Thr
                85                  90                  95

Ile Ala Asn Ile Tyr Thr Thr Gln His Arg Leu Asp Gln Gly Glu Ile
            100                 105                 110

Ser Ala Gly Asp Ala Ala Val Val Met Thr Ser Ala Gln Ile Thr Met
        115                 120                 125

Gly Met Pro Tyr Ala Val Thr Asp Ala Val Leu Ala Pro His Val Gly
    130                 135                 140

Gly Glu Ala Gly Ser Ser His Ala Pro Pro Ala Leu Thr Leu Ile
145                 150                 155                 160

Phe Asp Arg His Pro Ile Ala Ala Leu Leu Cys Tyr Pro Ala Ala Arg
                165                 170                 175

Tyr Leu Met Gly Ser Met Thr Pro Gln Ala Val Leu Ala Phe Val Ala
            180                 185                 190

Leu Ile Pro Pro Thr Leu Pro Gly Thr Asn Ile Val Leu Gly Ala Leu
        195                 200                 205

Pro Glu Asp Arg His Ile Asp Arg Leu Ala Lys Arg Gln Arg Pro Gly
    210                 215                 220

Glu Arg Leu Asp Leu Ala Met Leu Ala Ala Ile Arg Arg Val Tyr Gly
225                 230                 235                 240

Leu Leu Ala Asn Thr Val Arg Tyr Leu Gln Gly Gly Gly Ser Trp Trp
                245                 250                 255

Glu Asp Trp Gly Gln Leu Ser Gly Thr Ala Val Pro Gln Gly Ala
            260                 265                 270

Glu Pro Gln Ser Asn Ala Gly Pro Arg Pro His Ile Gly Asp Thr Leu
        275                 280                 285

Phe Thr Leu Phe Arg Ala Pro Glu Leu Leu Ala Pro Asn Gly Asp Leu
    290                 295                 300

Tyr Asn Val Phe Ala Trp Ala Leu Asp Val Leu Ala Lys Arg Leu Arg
305                 310                 315                 320

Pro Met His Val Phe Ile Leu Asp Tyr Asp Gln Ser Pro Ala Gly Cys
                325                 330                 335

Arg Asp Ala Leu Leu Gln Leu Thr Ser Gly Met Val Gln Thr His Val
            340                 345                 350

Thr Thr Pro Gly Ser Ile Pro Thr Ile Cys Asp Leu Ala Arg Thr Phe
        355                 360                 365

Ala Arg Glu Met Gly Glu Ala Asn
    370                 375

<210> SEQ ID NO 2
<211> LENGTH: 330
<212> TYPE: PRT
<213> ORGANISM: Artificial Sequence
<220> FEATURE:
```

<223> OTHER INFORMATION: 1-330 aa fragment of HSV1-TK (OTS-412)

<400> SEQUENCE: 2

```
Met Ala Ser Tyr Pro Cys His Gln His Ala Ser Ala Phe Asp Gln Ala
1               5                   10                  15

Ala Arg Ser Arg Gly His Ser Asn Arg Arg Thr Ala Leu Arg Pro Arg
            20                  25                  30

Arg Gln Gln Glu Ala Thr Glu Val Arg Leu Glu Gln Lys Met Pro Thr
        35                  40                  45

Leu Leu Arg Val Tyr Ile Asp Gly Pro His Gly Met Gly Lys Thr Thr
    50                  55                  60

Thr Thr Gln Leu Leu Val Ala Leu Gly Ser Arg Asp Asp Ile Val Tyr
65                  70                  75                  80

Val Pro Glu Pro Met Thr Tyr Trp Gln Val Leu Gly Ala Ser Glu Thr
                85                  90                  95

Ile Ala Asn Ile Tyr Thr Thr Gln His Arg Leu Asp Gln Gly Glu Ile
            100                 105                 110

Ser Ala Gly Asp Ala Ala Val Val Met Thr Ser Ala Gln Ile Thr Met
        115                 120                 125

Gly Met Pro Tyr Ala Val Thr Asp Ala Val Leu Ala Pro His Val Gly
130                 135                 140

Gly Glu Ala Gly Ser Ser His Ala Pro Pro Ala Leu Thr Leu Ile
145                 150                 155                 160

Phe Asp Arg His Pro Ile Ala Ala Leu Leu Cys Tyr Pro Ala Ala Arg
                165                 170                 175

Tyr Leu Met Gly Ser Met Thr Pro Gln Ala Val Leu Ala Phe Val Ala
            180                 185                 190

Leu Ile Pro Pro Thr Leu Pro Gly Thr Asn Ile Val Leu Gly Ala Leu
        195                 200                 205

Pro Glu Asp Arg His Ile Asp Arg Leu Ala Lys Arg Gln Arg Pro Gly
    210                 215                 220

Glu Arg Leu Asp Leu Ala Met Leu Ala Ala Ile Arg Arg Val Tyr Gly
225                 230                 235                 240

Leu Leu Ala Asn Thr Val Arg Tyr Leu Gln Gly Gly Gly Ser Trp Trp
                245                 250                 255

Glu Asp Trp Gly Gln Leu Ser Gly Thr Ala Val Pro Pro Gln Gly Ala
            260                 265                 270

Glu Pro Gln Ser Asn Ala Gly Pro Arg Pro His Ile Gly Asp Thr Leu
        275                 280                 285

Phe Thr Leu Phe Arg Ala Pro Glu Leu Leu Ala Pro Asn Gly Asp Leu
    290                 295                 300

Tyr Asn Val Phe Ala Trp Ala Leu Asp Val Leu Ala Lys Arg Leu Arg
305                 310                 315                 320

Pro Met His Val Phe Ile Leu Asp Tyr Asp
                325                 330
```

<210> SEQ ID NO 3
<211> LENGTH: 277
<212> TYPE: PRT
<213> ORGANISM: Artificial Sequence
<220> FEATURE:
<223> OTHER INFORMATION: 1-277 aa fragment of HSV1-TK(OTS-411)

<400> SEQUENCE: 3

```
Met Ala Ser Tyr Pro Cys His Gln His Ala Ser Ala Phe Asp Gln Ala
1               5                   10                  15
```

Ala Arg Ser Arg Gly His Ser Asn Arg Arg Thr Ala Leu Arg Pro Arg
            20                  25                  30

Arg Gln Gln Glu Ala Thr Glu Val Arg Leu Glu Gln Lys Met Pro Thr
        35                  40                  45

Leu Leu Arg Val Tyr Ile Asp Gly Pro His Gly Met Gly Lys Thr Thr
    50                  55                  60

Thr Thr Gln Leu Leu Val Ala Leu Gly Ser Arg Asp Asp Ile Val Tyr
65                  70                  75                  80

Val Pro Glu Pro Met Thr Tyr Trp Gln Val Leu Gly Ala Ser Glu Thr
                85                  90                  95

Ile Ala Asn Ile Tyr Thr Thr Gln His Arg Leu Asp Gln Gly Glu Ile
            100                 105                 110

Ser Ala Gly Asp Ala Ala Val Val Met Thr Ser Ala Gln Ile Thr Met
        115                 120                 125

Gly Met Pro Tyr Ala Val Thr Asp Ala Val Leu Ala Pro His Val Gly
    130                 135                 140

Gly Glu Ala Gly Ser Ser His Ala Pro Pro Ala Leu Thr Leu Ile
145                 150                 155                 160

Phe Asp Arg His Pro Ile Ala Ala Leu Leu Cys Tyr Pro Ala Ala Arg
                165                 170                 175

Tyr Leu Met Gly Ser Met Thr Pro Gln Ala Val Leu Ala Phe Val Ala
            180                 185                 190

Leu Ile Pro Pro Thr Leu Pro Gly Thr Asn Ile Val Leu Gly Ala Leu
        195                 200                 205

Pro Glu Asp Arg His Ile Asp Arg Leu Ala Lys Arg Gln Arg Pro Gly
    210                 215                 220

Glu Arg Leu Asp Leu Ala Met Leu Ala Ala Ile Arg Arg Val Tyr Gly
225                 230                 235                 240

Leu Leu Ala Asn Thr Val Arg Tyr Leu Gln Gly Gly Gly Ser Trp Trp
                245                 250                 255

Glu Asp Trp Gly Gln Leu Ser Gly Thr Ala Val Pro Pro Gln Gly Ala
            260                 265                 270

Glu Pro Gln Ser Asn
        275

<210> SEQ ID NO 4
<211> LENGTH: 306
<212> TYPE: PRT
<213> ORGANISM: Artificial Sequence
<220> FEATURE:
<223> OTHER INFORMATION: 1-306 aa fragment of HSV1-TK(OTS-411a)

<400> SEQUENCE: 4

Met Ala Ser Tyr Pro Cys His Gln His Ala Ser Ala Phe Asp Gln Ala
1               5                   10                  15

Ala Arg Ser Arg Gly His Ser Asn Arg Arg Thr Ala Leu Arg Pro Arg
            20                  25                  30

Arg Gln Gln Glu Ala Thr Glu Val Arg Leu Glu Gln Lys Met Pro Thr
        35                  40                  45

Leu Leu Arg Val Tyr Ile Asp Gly Pro His Gly Met Gly Lys Thr Thr
    50                  55                  60

Thr Thr Gln Leu Leu Val Ala Leu Gly Ser Arg Asp Asp Ile Val Tyr
65                  70                  75                  80

Val Pro Glu Pro Met Thr Tyr Trp Gln Val Leu Gly Ala Ser Glu Thr
                85                  90                  95

```
Ile Ala Asn Ile Tyr Thr Thr Gln His Arg Leu Asp Gln Gly Glu Ile
            100                 105                 110

Ser Ala Gly Asp Ala Ala Val Val Met Thr Ser Ala Gln Ile Thr Met
        115                 120                 125

Gly Met Pro Tyr Ala Val Thr Asp Ala Val Leu Ala Pro His Val Gly
130                 135                 140

Gly Glu Ala Gly Ser Ser His Ala Pro Pro Ala Leu Thr Leu Ile
145                 150                 155                 160

Phe Asp Arg His Pro Ile Ala Ala Leu Leu Cys Tyr Pro Ala Ala Arg
                165                 170                 175

Tyr Leu Met Gly Ser Met Thr Pro Gln Ala Val Leu Ala Phe Val Ala
            180                 185                 190

Leu Ile Pro Pro Thr Leu Pro Gly Thr Asn Ile Val Leu Gly Ala Leu
        195                 200                 205

Pro Glu Asp Arg His Ile Asp Arg Leu Ala Lys Arg Gln Arg Pro Gly
210                 215                 220

Glu Arg Leu Asp Leu Ala Met Leu Ala Ala Ile Arg Arg Val Tyr Gly
225                 230                 235                 240

Leu Leu Ala Asn Thr Val Arg Tyr Leu Gln Gly Gly Gly Ser Trp Trp
                245                 250                 255

Glu Asp Trp Gly Gln Leu Ser Gly Thr Ala Val Pro Pro Gln Gly Ala
            260                 265                 270

Glu Pro Gln Ser Asn Ala Gly Pro Arg Pro His Ile Gly Asp Thr Leu
        275                 280                 285

Phe Thr Leu Phe Arg Ala Pro Glu Leu Leu Ala Pro Asn Gly Asp Leu
290                 295                 300

Tyr Asn
305

<210> SEQ ID NO 5
<211> LENGTH: 346
<212> TYPE: PRT
<213> ORGANISM: Artificial Sequence
<220> FEATURE:
<223> OTHER INFORMATION: 1-346 aa fragment of HSV1-TK(OTS-411b)

<400> SEQUENCE: 5

Met Ala Ser Tyr Pro Cys His Gln His Ala Ser Ala Phe Asp Gln Ala
1               5                   10                  15

Ala Arg Ser Arg Gly His Ser Asn Arg Arg Thr Ala Leu Arg Pro Arg
            20                  25                  30

Arg Gln Gln Glu Ala Thr Glu Val Arg Leu Glu Gln Lys Met Pro Thr
        35                  40                  45

Leu Leu Arg Val Tyr Ile Asp Gly Pro His Gly Met Gly Lys Thr Thr
50                  55                  60

Thr Thr Gln Leu Leu Val Ala Leu Gly Ser Arg Asp Asp Ile Val Tyr
65                  70                  75                  80

Val Pro Glu Pro Met Thr Tyr Trp Gln Val Leu Gly Ala Ser Glu Thr
                85                  90                  95

Ile Ala Asn Ile Tyr Thr Thr Gln His Arg Leu Asp Gln Gly Glu Ile
            100                 105                 110

Ser Ala Gly Asp Ala Ala Val Val Met Thr Ser Ala Gln Ile Thr Met
        115                 120                 125

Gly Met Pro Tyr Ala Val Thr Asp Ala Val Leu Ala Pro His Val Gly
130                 135                 140
```

-continued

```
Gly Glu Ala Gly Ser Ser His Ala Pro Pro Ala Leu Thr Leu Ile
145                 150                 155                 160

Phe Asp Arg His Pro Ile Ala Ala Leu Leu Cys Tyr Pro Ala Ala Arg
                165                 170                 175

Tyr Leu Met Gly Ser Met Thr Pro Gln Ala Val Leu Ala Phe Val Ala
            180                 185                 190

Leu Ile Pro Pro Thr Leu Pro Gly Thr Asn Ile Val Leu Gly Ala Leu
        195                 200                 205

Pro Glu Asp Arg His Ile Asp Arg Leu Ala Lys Arg Gln Arg Pro Gly
    210                 215                 220

Glu Arg Leu Asp Leu Ala Met Leu Ala Ala Ile Arg Arg Val Tyr Gly
225                 230                 235                 240

Leu Leu Ala Asn Thr Val Arg Tyr Leu Gln Gly Gly Gly Ser Trp Trp
                245                 250                 255

Glu Asp Trp Gly Gln Leu Ser Gly Thr Ala Val Pro Pro Gln Gly Ala
            260                 265                 270

Glu Pro Gln Ser Asn Ala Gly Pro Arg Pro His Ile Gly Asp Thr Leu
        275                 280                 285

Phe Thr Leu Phe Arg Ala Pro Glu Leu Leu Ala Pro Asn Gly Asp Leu
    290                 295                 300

Tyr Asn Val Phe Ala Trp Ala Leu Asp Val Leu Ala Lys Arg Leu Arg
305                 310                 315                 320

Pro Met His Val Phe Ile Leu Asp Tyr Asp Gln Ser Pro Ala Gly Cys
                325                 330                 335

Arg Asp Ala Leu Leu Gln Leu Thr Ser Gly
            340                 345

<210> SEQ ID NO 6
<211> LENGTH: 352
<212> TYPE: PRT
<213> ORGANISM: Artificial Sequence
<220> FEATURE:
<223> OTHER INFORMATION: 1-352 aa fragment of HSV1-TK(OTS-411c)

<400> SEQUENCE: 6

Met Ala Ser Tyr Pro Cys His Gln His Ala Ser Ala Phe Asp Gln Ala
1               5                   10                  15

Ala Arg Ser Arg Gly His Ser Asn Arg Arg Thr Ala Leu Arg Pro Arg
            20                  25                  30

Arg Gln Gln Glu Ala Thr Glu Val Arg Leu Glu Gln Lys Met Pro Thr
        35                  40                  45

Leu Leu Arg Val Tyr Ile Asp Gly Pro His Gly Met Gly Lys Thr Thr
    50                  55                  60

Thr Thr Gln Leu Leu Val Ala Leu Gly Ser Arg Asp Asp Ile Val Tyr
65                  70                  75                  80

Val Pro Glu Pro Met Thr Tyr Trp Gln Val Leu Gly Ala Ser Glu Thr
                85                  90                  95

Ile Ala Asn Ile Tyr Thr Thr Gln His Arg Leu Asp Gln Gly Glu Ile
            100                 105                 110

Ser Ala Gly Asp Ala Ala Val Val Met Thr Ser Ala Gln Ile Thr Met
        115                 120                 125

Gly Met Pro Tyr Ala Val Thr Asp Ala Val Leu Ala Pro His Val Gly
    130                 135                 140

Gly Glu Ala Gly Ser Ser His Ala Pro Pro Ala Leu Thr Leu Ile
145                 150                 155                 160
```

```
Phe Asp Arg His Pro Ile Ala Ala Leu Leu Cys Tyr Pro Ala Ala Arg
                165                 170                 175

Tyr Leu Met Gly Ser Met Thr Pro Gln Ala Val Leu Ala Phe Val Ala
            180                 185                 190

Leu Ile Pro Pro Thr Leu Pro Gly Thr Asn Ile Val Leu Gly Ala Leu
        195                 200                 205

Pro Glu Asp Arg His Ile Asp Arg Leu Ala Lys Arg Gln Arg Pro Gly
    210                 215                 220

Glu Arg Leu Asp Leu Ala Met Leu Ala Ala Ile Arg Arg Val Tyr Gly
225                 230                 235                 240

Leu Leu Ala Asn Thr Val Arg Tyr Leu Gln Gly Gly Gly Ser Trp Trp
                245                 250                 255

Glu Asp Trp Gly Gln Leu Ser Gly Thr Ala Val Pro Pro Gln Gly Ala
            260                 265                 270

Glu Pro Gln Ser Asn Ala Gly Pro Arg Pro His Ile Gly Asp Thr Leu
        275                 280                 285

Phe Thr Leu Phe Arg Ala Pro Glu Leu Leu Ala Pro Asn Gly Asp Leu
    290                 295                 300

Tyr Asn Val Phe Ala Trp Ala Leu Asp Val Leu Ala Lys Arg Leu Arg
305                 310                 315                 320

Pro Met His Val Phe Ile Leu Asp Tyr Asp Gln Ser Pro Ala Gly Cys
                325                 330                 335

Arg Asp Ala Leu Leu Gln Leu Thr Ser Gly Met Val Gln Thr His Val
            340                 345                 350

<210> SEQ ID NO 7
<211> LENGTH: 227
<212> TYPE: PRT
<213> ORGANISM: Artificial Sequence
<220> FEATURE:
<223> OTHER INFORMATION: 227 aa fragment of HSV1-TK

<400> SEQUENCE: 7

Met Ala Ser Tyr Pro Cys His Gln His Ala Ser Ala Phe Asp Gln Ala
1               5                   10                  15

Ala Arg Ser Arg Gly His Ser Asn Arg Arg Thr Ala Leu Arg Pro Arg
            20                  25                  30

Arg Gln Gln Glu Ala Thr Glu Val Arg Leu Glu Gln Lys Met Pro Thr
        35                  40                  45

Leu Leu Arg Val Tyr Ile Asp Gly Pro His Gly Met Gly Lys Thr Thr
    50                  55                  60

Thr Thr Gln Leu Leu Val Ala Leu Gly Ser Arg Asp Asp Ile Val Tyr
65                  70                  75                  80

Val Pro Glu Pro Met Thr Tyr Trp Gln Val Leu Gly Ala Ser Glu Thr
                85                  90                  95

Ile Ala Asn Ile Tyr Thr Thr Gln His Arg Leu Asp Gln Gly Glu Ile
            100                 105                 110

Ser Ala Gly Asp Ala Ala Val Val Met Thr Ser Ala Gln Ile Thr Met
        115                 120                 125

Gly Met Pro Tyr Ala Val Thr Asp Ala Val Leu Ala Pro His Val Gly
    130                 135                 140

Gly Gly Gly Trp Glu Phe Thr Cys Pro Ala Pro Gly Pro His Pro His
145                 150                 155                 160

Leu Arg Pro Pro Ser His Arg Arg Pro Pro Val Leu Pro Gly Arg Ala
                165                 170                 175
```

```
Ile Pro Tyr Gly Gln His Asp Pro Pro Gly Arg Ala Gly Val Arg Gly
            180                 185                 190

Pro His Pro Ala Asp Leu Ala Arg His Lys His Arg Val Gly Gly Pro
        195                 200                 205

Ser Gly Gly Gln Thr His Arg Pro Pro Gly Gln Thr Pro Ala Pro Arg
    210                 215                 220

Arg Ala Ala
225

<210> SEQ ID NO 8
<211> LENGTH: 181
<212> TYPE: PRT
<213> ORGANISM: Artificial Sequence
<220> FEATURE:
<223> OTHER INFORMATION: 181 aa fragment of HSV1-TK

<400> SEQUENCE: 8

Met Ala Ser Tyr Pro Cys His Gln His Ala Ser Ala Phe Asp Gln Ala
1               5                   10                  15

Ala Arg Ser Arg Gly His Ser Asn Arg Arg Thr Ala Leu Arg Pro Arg
            20                  25                  30

Arg Gln Gln Glu Ala Thr Glu Val Arg Leu Glu Gln Lys Met Pro Thr
        35                  40                  45

Leu Leu Arg Val Tyr Ile Asp Gly Pro His Gly Met Gly Lys Thr Thr
    50                  55                  60

Thr Thr Gln Leu Leu Val Ala Leu Gly Ser Arg Asp Asp Ile Val Tyr
65                  70                  75                  80

Val Pro Glu Pro Met Thr Tyr Trp Gln Val Leu Gly Ala Ser Glu Thr
                85                  90                  95

Ile Ala Asn Ile Tyr Thr Thr Gln His Arg Leu Asp Gln Gly Glu Ile
            100                 105                 110

Ser Ala Gly Asp Ala Ala Val Val Met Thr Ser Ala Gln Ile Thr Met
        115                 120                 125

Gly Met Pro Tyr Ala Val Thr Asp Ala Val Leu Ala Pro His Val Gly
    130                 135                 140

Gly Arg Leu Gly Val His Met Pro Arg Pro Arg Pro Ser Pro Ser Ser
145                 150                 155                 160

Ser Thr Ala Ile Pro Ser Pro Ser Cys Ala Thr Arg Pro Arg Asp
                165                 170                 175

Thr Leu Trp Ala Ala
            180

<210> SEQ ID NO 9
<211> LENGTH: 993
<212> TYPE: DNA
<213> ORGANISM: Artificial Sequence
<220> FEATURE:
<223> OTHER INFORMATION: nucleotide sequence for 330 aa fragment of
      HSV1-TK (OTS-412)

<400> SEQUENCE: 9
ttagtcgtaa tccaggataa agacgtgcat gggacggagg cgtttggcca agacgtccaa      60
ggcccaggca aacacgttat acaggtcgcc gttgggggcc agcaactcgg gggcccgaaa     120
cagggtaaat aacgtgtccc cgatatgggg tcgtgggccc gcgttgctct ggggctcggc     180
acccctgggc ggcacggccg tccccgaaag ctgtccccaa tcctcccacc cgacccgcc     240 gccctgcaga taccgcaccg tattggcaag cagcccgtaa acgcggcgaa tcgcggccag     300
```

```
catagccagg tcaagccgct cgccggggcg ctggcgtttg gccaggcggt cgatgtgtct    360
gtcctccgga agggccccca acacgatgtt tgtgccgggc aaggtcggcg ggatgagggc    420
cacgaacgcc agcacggcct gggggtcat gctgcccata aggtatcgcg cggccgggta    480
gcacaggagg gcggcgatgg gatggcggtc gaagatgagg gtgagggccg ggggcggggc    540
atgtgaactc ccagcctccc ccccgacatg aggagccaga acggcgtcgg tcacggcata    600
aggcatgccc attgttatct gggcgcttgt cattaccacc gccgcgtccc cggccgatat    660
ctcaccctgg tcgaggcggt gttgtgtggt gtagatgttc gcgattgtct cggaagcccc    720
cagcacctgc cagtaagtca tcggctcggg tacgtagacg atatcgtcgc gcgaacccag    780
ggccaccagc agttgcgtgg tggtggtttt ccccatcccg tgaggaccgt ctatataaac    840
ccgcagtagc gtgggcattt tctgctccag gcggacttcc gtggcttctt gctgccggcg    900
agggcgcaac gccgtacgtc ggttgctatg gccgcgagaa cgcgcagcct ggtcgaacgc    960
agacgcgtgt tgatggcagg ggtacgaagc cat                                993

<210> SEQ ID NO 10
<211> LENGTH: 684
<212> TYPE: DNA
<213> ORGANISM: Artificial Sequence
<220> FEATURE:
<223> OTHER INFORMATION: nucleotide sequence for 227 aa fragment of
      HSV1-TK

<400> SEQUENCE: 10
atggcttcgt acccctgcca tcaacacgcg tctgcgttcg accaggctgc gcgttctcgc     60
ggccatagca accgacgtac ggcgttgcgc cctcgccggc agcaagaagc cacggaagtc    120
cgcctggagc agaaaatgcc cacgctactg cgggtttata tagacggtcc tcacgggatg    180
gggaaaacca ccaccacgca actgctggtg gccctgggtt cgcgcgacga tatcgtctac    240
gtacccgagc cgatgactta ctggcaggtg ctgggggctt ccgagacaat cgcgaacatc    300
tacaccacac aacaccgcct cgaccagggt gagatatcgg ccggggacgc ggcggtggta    360
atgacaagcg cccagataac aatgggcatg ccttatgccg tgaccgacgc cgttctggct    420
cctcatgtcg ggggggagg ctgggagttc acatgccccg ccccggccc tcaccctcat    480 cttcgaccgc catcccatcg ccgccctcct gtgctacccg gccgcgcgat accttatggg    540
cagcatgacc ccccaggccg tgctggcgtt cgtggccctc atcccgccga ccttgcccgg    600
cacaaacatc gtgttggggg cccttccgga ggacagacac atcgaccgcc tggccaaacg    660
ccagcgcccc ggcgagcggc ttga                                           684

<210> SEQ ID NO 11
<211> LENGTH: 546
<212> TYPE: DNA
<213> ORGANISM: Artificial Sequence
<220> FEATURE:
<223> OTHER INFORMATION: nucleotide sequence for 181 aa fragment of
      HSV1-TK

<400> SEQUENCE: 11
atggcttcgt acccctgcca tcaacacgcg tctgcgttcg accaggctgc gcgttctcgc     60
ggccatagca accgacgtac ggcgttgcgc cctcgccggc agcaagaagc cacggaagtc    120
cgcctggagc agaaaatgcc cacgctactg cgggtttata tagacggtcc tcacgggatg    180
gggaaaacca ccaccacgca actgctggtg gccctgggtt cgcgcgacga tatcgtctac    240
```

```
gtacccgagc cgatgactta ctggcaggtg ctgggggctt ccgagacaat cgcgaacatc    300
tacaccacac aacaccgcct cgaccagggt gagatatcgg ccggggacgc ggcggtggta    360
atgacaagcg cccagataac aatgggcatg ccttatgccg tgaccgacgc cgttctggct    420
cctcatgtcg gggggaggct gggagttcac atgccccgcc cccggccctc accctcatct    480
tcgaccgcca tcccatcgcc gccctcctgt gctacccggc cgcgcgatac cttatgggca    540
gcatga                                                              546
```

ONCOLYTIC VIRUS IMPROVED IN SAFETY AND ANTICANCER EFFECT

CROSS REFERENCE TO RELATED APPLICATIONS

This application is a National Stage of International Application No. PCT/KR2018/016874 filed Dec. 28, 2018, claiming priority based on U.S. Patent Application 62/611,174 filed Dec. 28, 2017 and Korean Patent Application No. 10-2018-0106841 filed Sep. 7, 2018.

TECHNICAL FIELD

The present invention relates to an oncolytic virus with improved safety and anticancer effect, and a use thereof.

BACKGROUND ART

With full-fledged use of gene recombination technologies, clinical studies using oncolytic viruses with increased tumor selectivity and anticancer efficacy have been initiated. The first recombinant oncolytic virus reported in literature is herpes simplex virus. Since then, researches on oncolysis using other viruses have been actively conducted (Martuza et al., 1991, Hwang et al., 2011; Kaufaman et al., 2015; Khuri et al., 2000; Park et al., 2008).

The usefulness of oncolytic viruses has got attention in earnest owing to the recent successful commercialization of herpes virus-based T-Vec (Talimogene laherparepvec) for treating advanced melanoma in the United States and Europe. Meanwhile, vaccinia virus lacking thymidine kinase (TK) gene has a great clinical utility, but there is a limit in maximizing its clinical effect due to its narrow therapeutic window. The narrow therapeutic range of TK-lacking vaccinia virus means that a high viral dose has a great clinical efficacy but entails clinical risks due to the toxicity of virus.

In fact, in a phase II clinical trial of Pexa-Vec (JX-594; SillaJen Inc.), which was conducted in thirty (30) patients with primary liver cancer, it was showed that the survival rate of a high dose group ($10^9$ pfu) increased as compared to the low dose group ($10^8$ pfu) (Heo et al., 2013). However, dose limiting toxicity (DLT) was observed at $3 \times 10^9$ pfu in phase I clinical trial conducted with intratumoral administration, thereby limiting the maximum tolerable dose (MTD) to $1 \times 10^9$ pfu. It has been reported that there was no relationship with drugs. However, there have been reported many cases of death shortly after the treatment with oncolytic viruses, indicating that undesirable virus replication may lead to unpredictable results. These dose-dependent increase in efficacy and dose-limiting toxicity imply that the development of a safer and more effective vaccinia virus is required.

On the other hand, ganciclovir (GCV) is an antiviral agent effective against herpes simplex virus, cytomegalovirus and varicella zoster virus. 5'-end of GCV is phosphorylated when combined with TK of herpes simplex virus, and then, converted into ganciclovir triphosphate (GCV-TP). GCV-TP inhibits the activity of viral DNA polymerase and attaches to the 3'-end of viral DNA, thereby terminating DNA elongation. GCV-TP is a highly toxic substance, and it can exhibit cytotoxicity by blocking DNA synthesis in cells.

These days, there are studies of using HSV-TK/GCV system in oncolytic virus therapy by inserting HSV-TK into an oncolytic virus to induce cancer cell apoptosis by co-administering GCV. In this therapy, first, the oncolytic virus infects tumor cells to induce a direct anticancer effect, and GCV phosphorylated by HSV1-TK (suicide gene) inhibits tumor cell proliferation, thereby exhibiting an additional anti-cancer effect (Oliver W et al, Human Gene Therapy, Vol. 10, No. 16, 1999). The HSV1-TK/GCV system was primarily used in oncolytic virus therapies that employ adenovirus as a vector. However, the additional cytotoxic effect expected by co-administering GCV is still controversial.

Specifically, it was observed that cytotoxic effect on glioma cells was significantly increased when replication-competent adenovirus armed with HSV-TK as administered in combination with GCV. However, not all studies were shown to have consistent result. (Lambright E S et al., Gene Ther, 8: 946-53). The reason for this was the HSV-TK/GCV system involves not only in viral replication but also in tumor cell proliferation that the total effects were offset due to the conflicting effect (Widner O, Morris J C, 2000).

Therefore, there is a need to study specific methods for securing safety, while simultaneously enhancing the anti-cancer effect, in applying the HSV-TK/GCV system in oncolytic virus therapies.

DISCLOSURE OF INVENTION

Technical Problem

Accordingly, the present inventors have conducted researches to develop an oncolytic virus having improved safety and anticancer effect, and have accomplished the present invention by developing a recombinant vaccinia virus comprising a gene (HSV1-TKmut) encoding a HSV1-TK fragment, in which a portion of C-terminal of HSV1-TK is truncated, or a variant thereof, and confirming that the recombinant vaccinia virus exhibits excellent safety and anticancer effect when administered in combination with GCV.

Solution to Problem

In order to achieve the above object, one aspect of the present invention provides a recombinant virus vector comprising a nucleotide sequence encoding an HSV-TK (herpes simplex virus thymidine kinase) fragment or a variant thereof.

Another aspect of the present invention provides an oncolytic virus comprising a nucleotide sequence encoding an HSV-TK fragment or a variant thereof.

A further aspect of the present invention provides a pharmaceutical composition for treating a cancer, which comprises the oncolytic virus.

A still further aspect of the present invention provides a pharmaceutical composition for treating a cancer, which comprises the oncolytic virus, and GCV (ganciclovir) or ACV (acyclovir) as active ingredients.

A still further aspect of the present invention provides a method for treating a cancer, which comprises administering the oncolytic virus, and GCV or ACV.

A still further aspect of the present invention provides a method for preparing a recombinant vaccinia virus, which comprises the steps of: i) transfecting a shuttle plasmid comprising a nucleotide sequence encoding an HSV-TK fragment or a variant thereof into a host cell, and treating the host cell with a wild type vaccinia virus; ii) culturing the host cell; and iii) obtaining the recombinant vaccinia virus from the culture.

A still further aspect of the present invention provides a use of the oncolytic virus for treating a cancer.

A still further aspect of the present invention provides a use of the pharmaceutical composition for treating a cancer.

A still further aspect of the present invention provides a use of the oncolytic virus for the manufacture of a medicament for treating a cancer.

A still further aspect of the present invention provides a use of the pharmaceutical composition for the manufacture of a medicament for treating a cancer.

Advantageous Effects of Invention

The oncolytic virus of the present invention with improved safety and anticancer effect is attributed to the encoding gene, HSV-TK fragment or a variant thereof, which was inserted into the deleted region of native TK gene of vaccinia virus. Further, the oncolytic virus of the present invention can express the HSV-TK fragment or the variant thereof to phosphorylate GCV, thereby killing the cancer cells infected with the oncolytic virus and even surrounding cancer cells. In addition, GCV also involves in the inhibition of virus replication, so that it can control the adverse side effects caused by virus in case when a high dose of virus is administered. Furthermore, although the number of viral particles decreases due to the suppression of virus replication by GCV, the anticancer effect increases. Therefore, the oncolytic virus of the present invention with improved safety and anticancer effect can be utilized for treating cancers.

BRIEF DESCRIPTION OF DRAWINGS

FIG. 11 is a graph showing the cell viability of A549 and NCI-H460 cancer cell lines, after administration of GCV, OTS-412, or in combination of OTS-412 and GCV, respectively.

FIG. 12 is a graph showing changes in tumor size over 12 days after administering saline, OTS-412, or a combination of OTS-412 and GCV to the mice transplanted with HCT-116 cancer cell line.

FIG. 13 is a bioluminescence image showing the distribution of OTS-412 in the mice transplanted with HCT-116 cancer cell line, taken after administering PBS, OTS-412, or a combination of OTS-412 and GCV to the mice.

FIG. 14 is a graph showing the virus DNA copy number counted in the tumor tissues obtained from the mice transplanted with HCT-116 cancer cell line, after administration of OTS-412 alone or in combination with GCV to the mice.

FIG. 15 is a graph showing changes in body weight over 12 days after administration of saline, OTS-412, or a combination of OTS-412 and GCV to the HCT-116 tumor-bearing mice.

FIG. 16 is a graph showing changes in tumor size over 24 days after administration of saline, OTS-412, or a combination of OTS-412 and GCV to the Renca tumor-bearing mice.

FIG. 17 is a graph showing the number of total virus particles in the tumor tissues obtained from the Renca tumor-bearing mice after administration of saline, OTS-412, or in combination of OTS-412 and GCV.

FIG. 18 is a TUNEL staining result of tumor tissue obtained from the mice transplanted with Renca cancer cell line, after administering saline, OTS-412, or a combination of OTS-412 and GCV to the mice.

FIG. 19 is a graph showing the quantification of apoptosis portion observed in TUNEL staining of the tumor tissue obtained from the mice transplanted with Renca cancer cell line, after administering saline, OTS-412, or a combination of OTS-412 and GCV to the mice.

FIG. 20 is a graph showing changes in tumor size over 21 days after administration of saline, OTS-412, or in combination of OTS-412 and GCV to HCT-116 tumor-bearing mice.

FIG. 21 is a immunohistochemistry (IHC) of the tumor tissue obtained from the mice transplanted with HCT-116 cancer cell line, after administering saline, OTS-412, or a combination of OTS-412 and GCV.

FIG. 22 is a graph showing the quantification of the stained portion observed in immunohistochemistry (IHC) of the tumor tissue obtained from the mice transplanted with HCT-116 cancer cell line, after administering saline, OTS-412, or a combination of OTS-412 and GCV.

FIG. 23 is a graph showing the quantification of the necrotic portion observed in H&E staining of the tumor tissue obtained from mice transplanted with HCT-116 cancer cell line, after administering saline, OTS-412, or a combination of OTS-412 and GCV.

FIG. 24 is a graph showing the viable tumor area by H&E staining of tumor tissues obtained from the HCT-116 tumor-bearing mice after administering saline, OTS-412, or a combination of OTS-412 and GCV to the mice.

FIG. 25 is a graph showing body weight of each group of mice treated with OTS-412 and GCV for 21 days of administering saline, OTS-412, or a combination of to the mice transplanted with HCT-116 cancer cell line.

FIG. 26 is a graph showing the cell viability assessment of thirteen (13) different cancer cell lines after treating with OTS-412.

FIG. 27 is a graph showing the IC$_{50}$ of OTS-412 administered in HCT-116, SK-MEL-28, and DU145 cancer cell lines.

FIG. 28 is a bioluminescence image showing the virus distribution of intraperitoneally injected OTS-412 in HCT-116 tumor-bearing mice on day 3 and day 7.

BEST MODE FOR CARRYING OUT THE INVENTION

Figure 1:
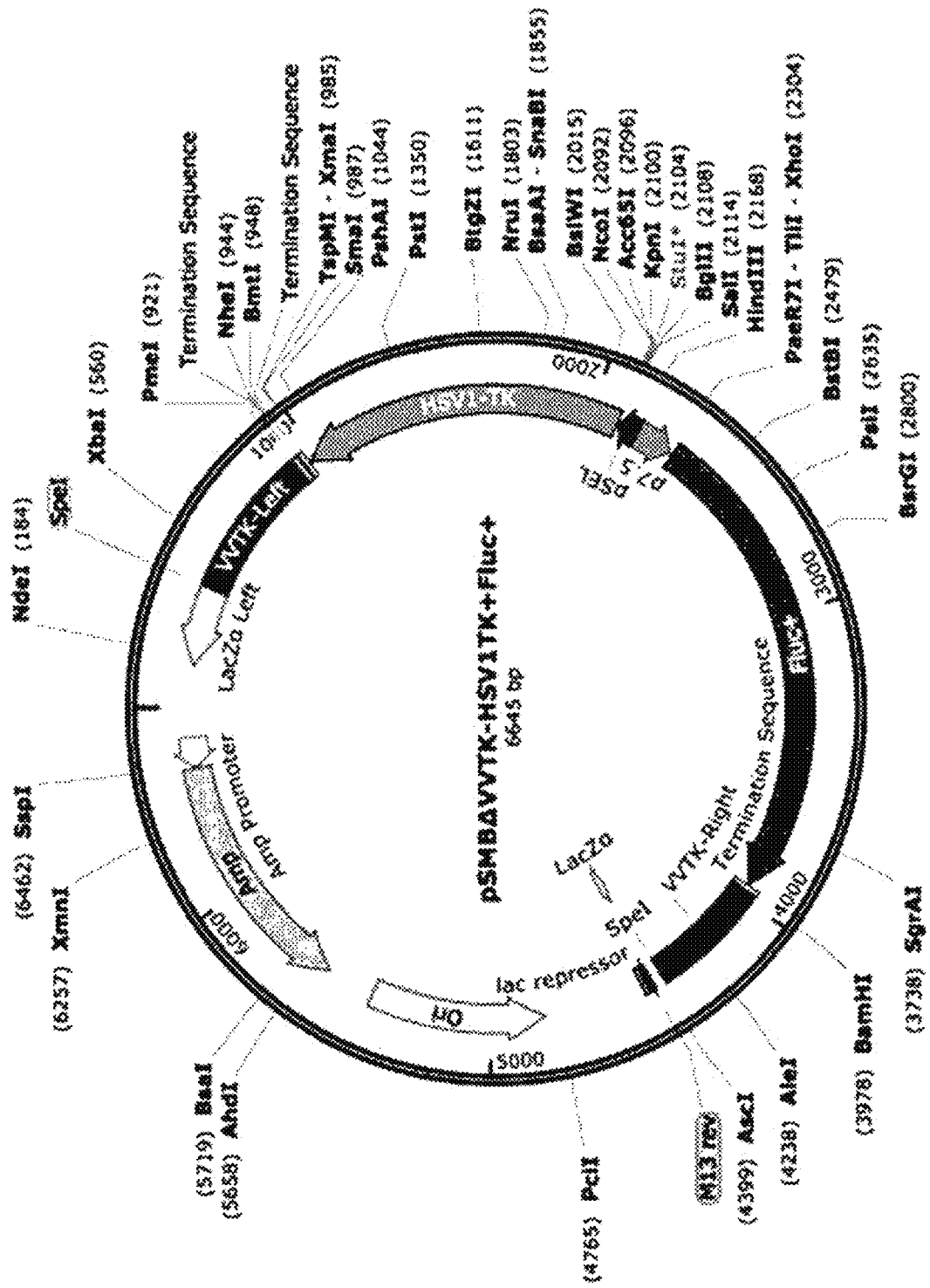
FIG. 1 is a schematic diagram of a shuttle plasmid vector carrying an HSV1-TK gene used to prepare recombinant vaccinia virus.

Hereinafter, the present invention will be described in detail.

The present invention provides a recombinant virus vector comprising a nucleotide sequence encoding an HSV-TK (herpes simplex virus thymidine kinase) fragment or a variant thereof.

The term "TK (thymidine kinase)" as used herein means thymidine kinase, an enzyme involved in the biosynthesis of nucleotides. The TK is an enzyme used for the biosynthesis of nucleotides in both of cells and viruses. The TK may be derived from herpes simplex virus. At this time, the herpes simplex virus may be herpes simplex virus type 1 (HSV1) or herpes simplex virus type 2 (HSV2).

The term "HSV-TK (herpes simplex virus thymidine kinase)" as used herein means the thymidine kinase enzyme of herpes simplex virus. Specifically, the HSV-TK may be HSV1-TK (herpes simplex virus type 1 thymidine kinase). The HSV1-TK is an enzyme involved in the initial phosphorylation reaction during DNA synthesis process in the herpes simplex virus. HSV-TK also involves in the phosphorylation of an antiviral agent, GCV (ganciclovir) or ACV (acyclovir). In particular, for GCV or ACV, HSV1-TK reacts around 10 times more sensitive than any other TKs present in other types of viruses.

The term "HSV-TK fragment" as used herein means a thing where some amino acid residues of HSV-TK are deleted. Specifically, the HSV-TK fragment may be the one where a portion of the N-terminal or C-terminal of HSV-TK is deleted. Preferably, the HSV-TK fragment may be the one where a portion of the C-terminal of HSV-TK is deleted. In one embodiment, the HSV-TK fragment may be the one where 1 to 195 amino acid residues from the C-terminal of HSV-TK are consecutively deleted. The HSV-TK fragment may be the one in which 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110, 120, 130, 140, 150, 160, 170, 180, 190, or 195 amino acid residues from the C-terminal of HSV-TK are consecutively deleted.

The HSV1-TK fragment or variant thereof of the present invention may be derived from a virus which is mutated by inducing adaptive evolution. In order to develop vaccinia viruses expressing an optimized HSV1-TK fragment or its variant, the present inventors have prepared a recombinant vaccinia virus containing the HSV1-TK gene and induced adaptive evolution in the absence of TK. The resulting recombinant vaccinia viruses were subjected to an experiment for confirming luciferase activity, genome analysis and an experiment for confirming sensitivity to GCV, and vaccinia virus OTS-412 expressing an HSV1-TK fragment or its variant has been screened. The HSV1-TK fragment or its variant retained sensitivity to GCV despite of the significant truncation at the C-terminal of HSV1-TK. Furthermore, it was confirmed that anticancer effect was increased when the vaccinia virus expressing the HSV1-TK fragment or its variant was administered in combination with GCV.

The HSV-TK fragment may be an HSV1-TK fragment. One embodiment of the HSV1-TK fragment may be any one of the fragments where 1 to 195, 24 to 149, or 30 to 46 amino acid residues from the C-terminal of the amino acid sequence represented by SEQ ID NO: 1 are consecutively deleted. Specifically, the HSV1-TK fragment may be the one where 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110, 120, 130, 140, 150, 160, 170, 180, 190, or 195 amino acid residues from the C-terminal of the amino acid sequence represented by SEQ ID NO: 1 are consecutively deleted. Preferably, the HSV1-TK fragment may be the one where 24, 30, 70, 99, 149, or 195 amino acid residues from the C-terminal of the amino acid sequence represented by SEQ ID NO: 1 are consecutively deleted. The HSV1-TK fragment may have a reduced sensitivity to GCV due to the deletion of some amino acid residues at the C-terminal.

One example of the HSV1-TK fragment may be the one where 195, 149, 99, 70, 46, 30, or 24 amino acid residues from the C-terminal of the amino acid sequence represented by SEQ ID NO: 1 are consecutively deleted. Specifically, the HSV1-TK fragment may have any one of the amino acid sequences selected from the group consisting of SEQ ID NOS: 2 to 6.

The nucleotide sequence encoding the HSV1-TK fragment may be a nucleotide sequence encoding any one of the HSV1-TK fragments where 1 to 195, 24 to 149, or 30 to 46 amino acid residues from the C-terminal of the amino acid sequence represented by SEQ ID NO: 1 are consecutively deleted. Specifically, the nucleotide sequence encoding the HSV1-TK fragment may be a nucleotide sequence encoding any one of the amino acid sequences selected from the group consisting of SEQ ID NOS: 2 to 6. Preferably, the nucleotide sequence encoding the HSV1-TK fragment may be the nucleotide sequence of SEQ ID NO: 9.

The variant of the HSV-TK fragment may be a variant of the HSV1-TK fragment. Specifically, the variant of the HSV1-TK fragment may be the one in which at least one of the amino acid residues constituting the HSV1-TK fragment is substituted. In particular, the variant of the HSV1-TK fragment may comprise $1^{st}$ to $145^{th}$ amino acid residues of the amino acid sequence of SEQ ID NO: 1. In one embodiment, the variant of the HSV1-TK fragment may have the amino acid sequence of SEQ ID NO: 7 or 8. The nucleotide sequence encoding the variant of the HSV1-TK fragment may be the nucleotide sequence of SEQ ID NO: 10 or 11.

The virus vector is a vector for introducing a gene into a cell or for producing a virus. The virus vector may be derived from adenovirus, herpes simplex virus, lentivirus, retrovirus, adeno-associated virus, vaccinia virus, or poxvirus.

Another aspect of the present invention provides an oncolytic virus comprising a nucleotide sequence encoding an HSV-TK fragment or a variant thereof.

The term "oncolytic virus" as used herein means a recombinant virus that destroys cancer cells, the gene of the virus being manipulated to replicate specifically in cancer cells. The oncolytic virus may be derived from adenovirus, herpes simplex virus, measles virus, lentivirus, retrovirus, cytomegalovirus, baculovirus, reovirus, adeno-associated virus, myxoma virus, vesicular stomatitis virus, poliovirus, Newcastle disease virus, parvovirus, coxsackie virus, senecavirus, vaccinia virus, or poxvirus. Preferably, the oncolytic virus may be derived from vaccinia virus.

The vaccinia virus may be Western Reserve (WR), NYVAC (New York Vaccinia Virus), Wyeth (The New York City Board of Health; NYCBOH), LC16m8, Lister, Copenhagen, Tian Tan, USSR, TashKent, Evans, IHD-J (International Health Division-J) or IHD-W (International Health Division-White) strain, but not limited thereto.

The HSV-TK fragment may be an HSV1-TK fragment. One embodiment of the HSV1-TK fragment may be any one of the fragments where 1 to 195, 24 to 149, or 30 to 46 amino acid residues from the C-terminal of the amino acid sequence represented by SEQ ID NO: 1 are consecutively deleted. Specifically, the HSV1-TK fragment may be the one where 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110, 120, 130, 140, 150, 160, 170, 180, 190, or 195 amino acid residues from the C-terminal of the amino acid sequence represented by SEQ ID NO: 1 are consecutively deleted. Preferably, the HSV1-TK fragment may be the one where 24, 30, 70, 99, 149, or 195 amino acid residues from the C-terminal of the amino acid sequence represented by SEQ ID NO: 1 are consecutively deleted. The HSV1-TK fragment may have a reduced sensitivity to GCV due to the deletion of some amino acid residues at the C-terminal.

One example of the HSV1-TK fragment may be the one where 195, 149, 99, 70, 46, 30, or 24 amino acid residues from the C-terminal of the amino acid sequence represented by SEQ ID NO: 1 are consecutively deleted. Specifically, the HSV1-TK fragment may have any one of the amino acid sequences selected from the group consisting of SEQ ID NOS: 2 to 6.

The nucleotide sequence encoding the HSV1-TK fragment may be a nucleotide sequence encoding any one of the HSV1-TK fragments where 1 to 195, 24 to 149, or 30 to 46 amino acid residues from the C-terminal of the amino acid sequence represented by SEQ ID NO: 1 are consecutively deleted. Specifically, the nucleotide sequence encoding the HSV1-TK fragment may be a nucleotide sequence encoding any one of the amino acid sequences selected from the group consisting of SEQ ID NOS: 2 to 6. Preferably, the nucleotide sequence encoding the HSV1-TK fragment may be the nucleotide sequence of SEQ ID NO: 9.

The variant of the HSV-TK fragment may be a variant of the HSV1-TK fragment. Specifically, the variant of the HSV1-TK fragment may be the one in which at least one of the amino acid residues constituting the HSV1-TK fragment is substituted. In particular, the variant of the HSV1-TK fragment may comprise $1^{st}$ to $145^{th}$ amino acid residues of the amino acid sequence of SEQ ID NO: 1. In one embodiment, the variant of the HSV1-TK fragment may have the amino acid sequence of SEQ ID NO: 7 or 8. The nucleotide sequence encoding the variant of the HSV1-TK fragment may be the nucleotide sequence of SEQ ID NO: 10 or 11.

The oncolytic virus may have native TK gene deleted. Specifically, the oncolytic virus may be the one where native TK gene is deleted by inserting or substituting the nucleotide sequence coding for the HSV1-TK fragment into the native TK gene region. In one embodiment of the present invention, the native TK gene of vaccinia virus was deleted by inserting a nucleotide sequence coding for an HSV1-TK fragment into the native TK gene region of vaccinia virus.

The term "gene defect" as used herein means that the gene is not expressed due to partial or entire deletion of the gene or insertion of a foreign gene into the gene. The partial gene deletion may be the partial deletion at the 5'-end or 3'-end. That is, the native TK gene of the oncolytic virus may be partially or entirely deleted.

Figure 6:
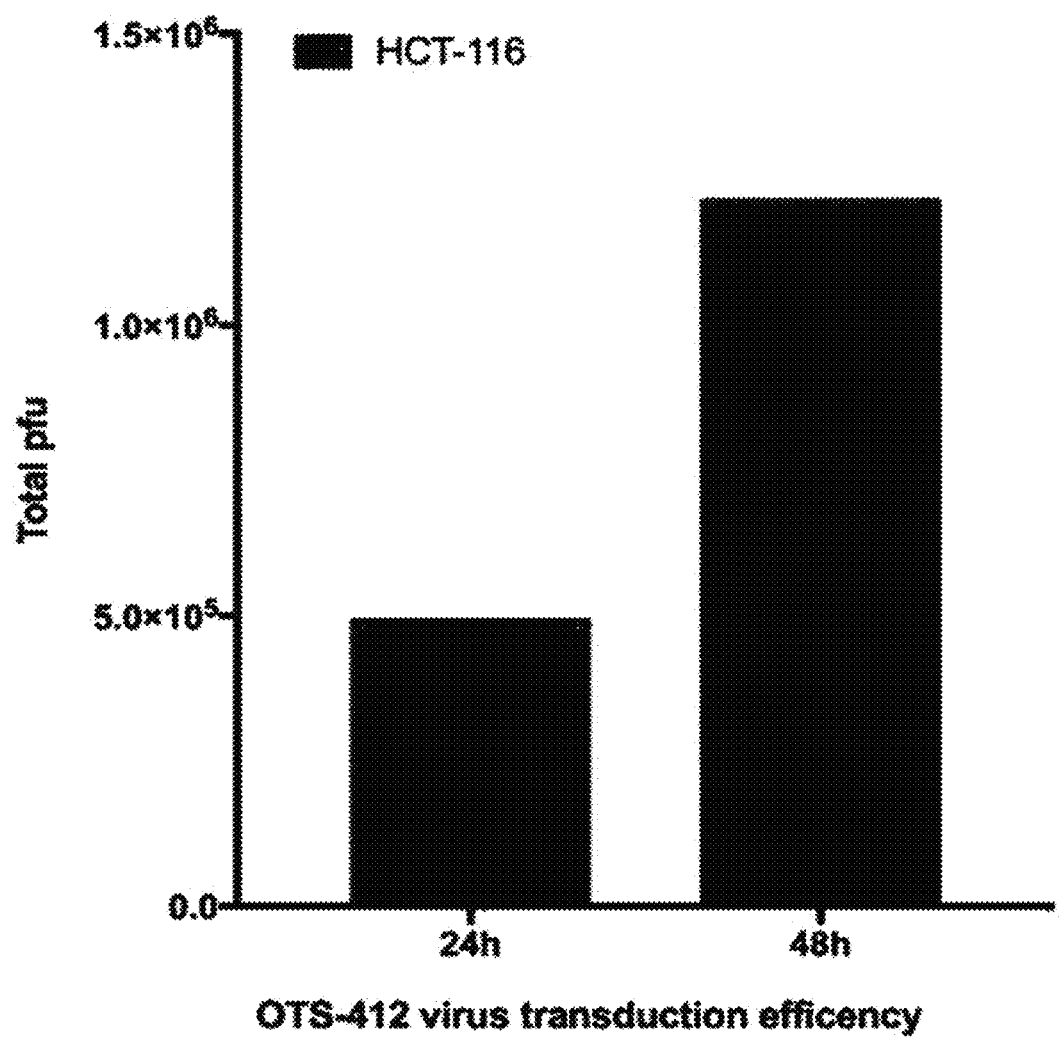
FIG. 6 is a graph showing replicability of OTS-412 after 24 and 48 hours of infection in HCT-116 cancer cell line.

In one example of the present invention, recombinant vaccinia virus OTS-412 comprising a gene coding for an HSV-TK fragment was infected into HCT-116 cancer cell lines, and the infection and replication efficiency were confirmed (FIG. 6). Further, OTS-412 was administered in thirteen (13) different cancer cell lines and, after culturing for 72 hours, the cell viability measured to show the cytotoxicity of OTS-412 (FIG. 26). Thus, the oncolytic virus of the present invention comprising a nucleotide sequence coding for an HSV-TK fragment can be usefully employed in treating a cancer.

A still further aspect of the present invention provides a pharmaceutical composition for preventing or treating a cancer, which comprises an oncolytic virus comprising a nucleotide sequence coding for an HSV-TK fragment or a variant thereof as an active ingredient.

The oncolytic virus contained in the pharmaceutical composition as an active ingredient is as described above.

The dosage of the oncolytic virus varies depending on the condition and body weight of individual, the severity of disease, the type of drug, the route and period of administration, and can be appropriately selected by a person skilled in the art. The dosage may be such that a patient receives $1\times10^3$ to $1\times10^{18}$ of virus particles, infectious virus units (TCID$_{50}$), or plaque forming units (pfu). Specifically, the dosage may be $1\times10^{10}$, $2\times10^3$, $5\times10^3$, $1\times10^4$, $2\times10^4$, $5\times10^4$, $1\times10^5$, $2\times10^5$, $5\times10^5$, $1\times10^6$, $2\times10^6$, $5\times10^6$, $1\times10^7$, $2\times10^7$, $5\times10^7$, $1\times10^8$, $2\times10^8$, $5\times10^8$, $1\times10^9$, $2\times10^9$, $5\times10^9$, $1\times10^{10}$, $5\times10^{10}$, $1\times10^{11}$, $5\times10^{11}$, $1\times10^{12}$, $1\times10^{13}$, $1\times10^{14}$, $1\times10^{15}$, $1\times10^{16}$, $1\times10^{17}$, $1\times10^{18}$, or more of virus particles, infectious virus units (TCID$_{50}$) or plaque forming units (pfu), in which various values and ranges therebetween can be included. Preferably, the oncolytic virus may be administered at a dosage of $1\times10^3$ to $1\times10^{10}$ pfu. In one example of the present invention, the oncolytic virus was administered at dosages of $1\times10^6$, $1\times10^7$ and $1\times10^8$ pfu.

The cancer may be selected from the group consisting of lung cancer, colorectal cancer, prostate cancer, thyroid cancer, breast cancer, brain cancer, head and neck cancer, esophageal cancer, skin cancer, thymic cancer, gastric cancer, colon cancer, liver cancer, ovarian cancer, uterine cancer, bladder cancer, rectal cancer, gallbladder cancer, biliary tract cancer, pancreatic cancer, non-small cell lung cancer, bone cancer, intraocular melanoma, perianal cancer, fallopian tube carcinoma, endometrial carcinoma, cervical cancer, vaginal carcinoma, vulvar carcinoma, Hodgkin's disease, small intestine cancer, endocrine adenocarcinoma, parathyroid cancer, adrenal cancer, soft tissue sarcoma, urethral cancer, penile cancer, chronic leukemia, acute leukemia, lymphocytic lymphoma, kidney cancer, ureteral cancer, renal cell carcinoma, renal pelvis carcinoma, central nervous system tumors, primary central nervous system lymphoma, spinal cord tumor, brainstem glioma, pituitary adenoma, and a combination thereof.

The pharmaceutical composition of the present invention may further comprise a physiologically acceptable carrier. In addition, the pharmaceutical composition of the present invention may further comprise suitable excipients and diluents conventionally used in the preparation of pharmaceutical compositions. In addition, it can be formulated in the form of an injection according to a conventional method.

The pharmaceutical composition may be formulated into sterilized aqueous solutions, non-aqueous solutions, suspensions, emulsions, freeze-dried preparations, suppositories, or the like for parenteral administration. For non-aqueous solution and suspension, propylene glycol, polyethylene glycol, vegetable oil such as olive oil, injectable ester such as ethyl oleate, and the like may be used. As the suppository base, Witepsol™, macrogol, Tween™61, cacao butter, laurin fat, glycerogelatin, and the like may be used.

The pharmaceutical composition may be administered to a subject in a variety of ways and amounts depending on the condition of the patient and the presence or absence of side effects, and the optimal way, dosage, and frequency of administration may be selected by a person skilled in the art within a suitable range. In addition, the pharmaceutical composition may be administered in combination with other drug or physiologically active substance of which therapeutic effect is known to the disease to be treated, or may be formulated in combination with other drugs.

The pharmaceutical composition may be administered parenterally, including intratumoral, intraperitoneal, subcutaneous, intra-dermal, intra-nodal and intravenous administration, and the like. Preferably, it can be intratumoral, intraperitoneal or intravenous administration. On the other hand, the dosage of the pharmaceutical composition may be determined according to the administration schedule, the dosage, and the health condition of the patient.

Figure 9:
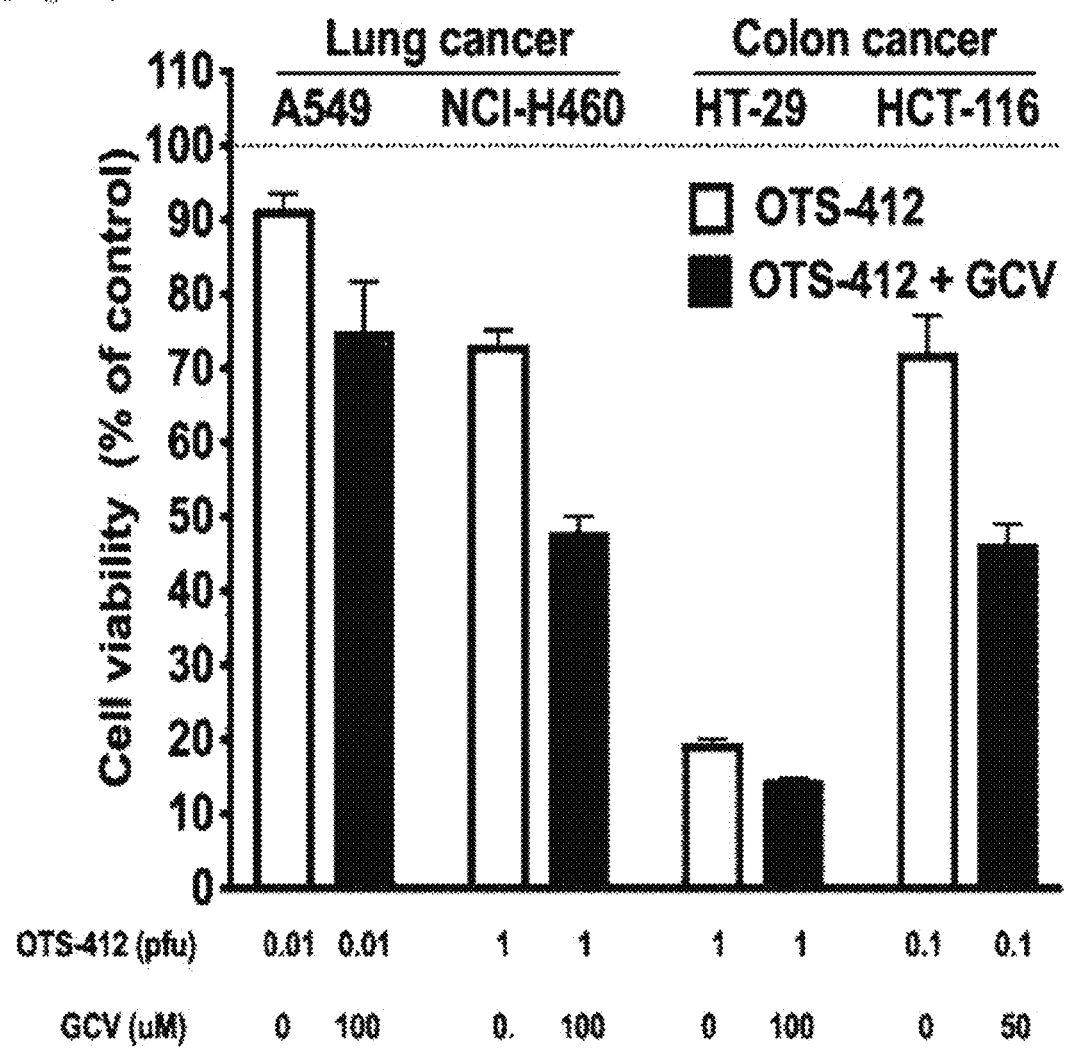
FIG. 9 is a graph showing the cell viability of A549, NCI-H460, HT-29, and HCT-116 cancer cell lines, after administration of OTS-412 alone or in combination with GCV, respectively.

The present inventors administered OTS-412 in combination with GCV in A549, NCI-H460, HT-29, and HCT-116 cancer cell lines and assessed the viability of the cancer cell lines, and confirmed the anticancer effect was increased by the combined treatment (FIG. 9). In addition, it was confirmed that even when OTS-412 and GCV were administered in combination to cancer cell lines, the virus maintained a certain level of replication capacity (FIG. 14). Thus, a combination of the oncolytic virus comprising a nucleotide sequence encoding an HSV-TK fragment or a variant thereof and GCV can be usefully used for treating a cancer.

A further aspect of the present invention provides a pharmaceutical composition for preventing or treating a cancer, which comprises an oncolytic virus comprising a nucleotide sequence coding for an HSV-TK fragment or a variant thereof, and GCV (ganciclovir) or ACV (acyclovir) as active ingredients.

The oncolytic virus and GCV or ACV contained in the pharmaceutical composition may be administered simultaneously, sequentially, or in reverse order. Specifically, the oncolytic virus and GCV or ACV contained in the pharmaceutical composition may be administered simultaneously. In addition, the oncolytic virus may be administered first, followed by GCV or ACV administration. In addition, the oncolytic virus is administered first, followed by GCV or ACV, and the oncolytic virus again.

The oncolytic virus contained in the pharmaceutical composition as an active ingredient is as described above.

The dosage of the oncolytic virus varies depending on the condition and body weight of individual, the severity of disease, the type of drug, the route and period of administration, and can be appropriately selected by a person skilled in the art. The dosage may be such that a patient receives $1 \times 10^3$ to $1 \times 10^{18}$ of virus particles, infectious virus units (TCID$_5$), or plaque forming units (pfu). Specifically, the dosage may be $1 \times 10^3$, $2 \times 10^3$, $5 \times 10^3$, $1 \times 10^4$, $2 \times 10^4$, $5 \times 10^4$, $1 \times 10^5$, $2 \times 10^5$, $5 \times 10^5$, $1 \times 10^6$, $2 \times 10^6$, $5 \times 10^6$, $1 \times 10^7$, $2 \times 10^7$, $5 \times 10^7$, $1 \times 10^8$, $2 \times 10$, $5 \times 10$, $1 \times 10^9$, $2 \times 10^9$, $5 \times 10^9$, $1 \times 10^{10}$, $5 \times 10^{10}$, $1 \times 10^{11}$, $5 \times 10^{11}$, $1 \times 10^{12}$, $1 \times 10^{13}$, $1 \times 10^{14}$, $1 \times 10^{15}$, $1 \times 10^{16}$, $1 \times 10^{17}$, $1 \times 10^{18}$, or more of virus particles, infectious virus units (TCID$_{50}$) or plaque forming units (pfu), in which various values and ranges therebetween can be included. Preferably, the oncolytic virus may be administered at a dosage of $1 \times 10^3$ to $1 \times 10^{10}$ pfu. In one example of the present invention, the oncolytic virus was administered at dosages of $1 \times 10^6$, $1 \times 10^7$ and $1 \times 10^8$ pfu.

The term "GCV" used herein means an antiviral agent, which is referred to as ganciclovir and is effective against herpes simplex virus, cytomegalovirus, and varicella zoster virus. GCV is phosphorylated at the 5'-end by TK of a virus and then converted into ganciclovir triphosphate (GCV-TP). GCV-TP inhibits the activity of viral DNA polymerase and attaches to the 3'-end of viral DNA, thereby terminating DNA elongation. In addition, phosphorylated GCV can stop cellular DNA replication, thereby inhibiting cell growth. GCV is represented by the following Formula 1.

[Formula 1]

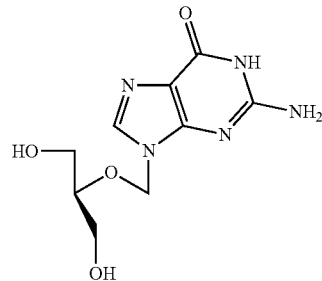

The term "ACV" used herein means an antiviral agent, which is referred to as acyclovir and is effective against herpes simplex virus, varicella zoster virus and Epstein-Barr virus. ACV is phosphorylated by TK of the virus and then converted into acyclovir triphosphate (ACV-TP). ACV-TP inhibits the activity of viral DNA polymerase and attaches to the 3'-end of viral DNA, thereby terminating DNA elongation. ACV is represented by the following Formula 2.

[Formula 2]

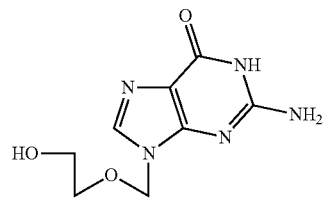

In addition, GCV or ACV may be administered at a daily dose of 0.1 µg/kg to 50 mg/kg. Specifically, the daily dose of GCV or ACV may be 0.1 µg/kg to 50 mg/kg, 1 µg/kg to 40 mg/kg, 5 µg/kg to 30 mg/kg, or 10 µg/kg to 20 mg/kg. In one example of the present invention, GCV was administered at a daily dose of 50 mg/kg.

The cancer may be selected from the group consisting of lung cancer, colorectal cancer, prostate cancer, thyroid cancer, breast cancer, brain cancer, head and neck cancer, esophageal cancer, skin cancer, thymic cancer, gastric cancer, colon cancer, liver cancer, ovarian cancer, uterine cancer, bladder cancer, rectal cancer, gallbladder cancer, biliary tract cancer, pancreatic cancer, non-small cell lung cancer, bone cancer, intraocular melanoma, perianal cancer, fallopian tube carcinoma, endometrial carcinoma, cervical cancer, vaginal carcinoma, vulvar carcinoma, Hodgkin's disease, small intestine cancer, endocrine adenocarcinoma, parathyroid cancer, adrenal cancer, soft tissue sarcoma, urethral cancer, penile cancer, chronic leukemia, acute leukemia, lymphocytic lymphoma, kidney cancer, ureteral cancer, renal cell carcinoma, renal pelvis carcinoma, central nervous system tumors, primary central nervous system lymphoma, spinal cord tumor, brainstem glioma, pituitary adenoma, and a combination thereof.

The pharmaceutical composition of the present invention may further comprise a physiologically acceptable carrier. In addition, the pharmaceutical composition of the present invention may further comprise suitable excipients and diluents conventionally used in the preparation of pharmaceutical compositions. In addition, it can be formulated in the form of an injection according to a conventional method.

The pharmaceutical composition may be formulated into sterilized aqueous solutions, non-aqueous solutions, suspensions, emulsions, freeze-dried preparations, suppositories, or the like for parenteral administration. For non-aqueous solution and suspension, propylene glycol, polyethylene glycol, vegetable oil such as olive oil, injectable ester such as ethyl oleate, and the like may be used. As the suppository base, Witepsol™, macrogol, Tween™61, cacao butter, laurin fat, glycerogelatin, and the like may be used.

The pharmaceutical composition may be administered to a subject in a variety of ways and amounts depending on the condition of the patient and the presence or absence of side effects, and the optimal way, dosage, and frequency of administration may be selected by a person skilled in the art within a suitable range. In addition, the pharmaceutical composition may be administered in combination with other drug or physiologically active substance of which therapeutic effect is known to the disease to be treated, or may be formulated in the form of a combination preparation with other drugs.

The pharmaceutical composition may be administered parenterally, including intratumoral, intraperitoneal, subcutaneous, intra-dermal, intra-nodal and intravenous administration, and the like. Preferably, it can be intratumoral, intraperitoneal or intravenous administration. On the other hand, the dosage of the pharmaceutical composition may be determined according to the administration schedule, the dosage, and the health condition of the patient.

A still further aspect of the present invention provides a method for treating a cancer, which comprises administering an oncolytic virus comprising a nucleotide sequence coding for an HSV-TK fragment or a variant thereof and GCV or ACV to an individual in need thereof.

The oncolytic virus, GCV and ACV are as described above.

The dosage of the oncolytic virus varies depending on the condition and body weight of individual, the severity of disease, the type of drug, the route and period of administration, and can be appropriately selected by a person skilled in the art. The dosage may be such that a patient receives $1\times10^3$ to $1\times10^{18}$ of virus particles, infectious virus units (TCID$_5$), or plaque forming units (pfu). Specifically, the dosage may be $1\times10^3$, $2\times10^3$, $5\times10^3$, $1\times10^4$, $2\times10^4$, $5\times10^4$, $1\times10^5$, $2\times10^5$, $5\times10^5$, $1\times10^6$, $2\times10^6$, $5\times10^6$, $1\times10^7$, $2\times10^7$, $5\times10^7$, $1\times10^8$, $2\times10^8$, $5\times10^8$, $1\times10^9$, $2\times10^9$, $5\times10^9$, $1\times10^{10}$, $5\times10^{10}$, $1\times10^{11}$, $5\times10^{11}$, $1\times10^{12}$, $1\times10^{13}$, $1\times10^{14}$, $1\times10^{15}$, $1\times10^{16}$, $1\times10^{17}$, $1\times10^{18}$, or more of virus particles, infectious virus units (TCID$_{50}$) or plaque forming units (pfu), in which various values and ranges therebetween can be included. Preferably, the oncolytic virus may be administered at a dosage of $1\times10^3$ to $1\times10^1$ pfu. In one example of the present invention, the oncolytic virus was administered at dosages of $1\times10^6$, $1\times10^7$ and $1\times10^8$ pfu.

In addition, GCV or ACV may be administered at a daily dose of 0.1 µg/kg to 50 mg/kg. Specifically, the daily dose of GCV or ACV may be 0.1 µg/kg to 50 mg/kg, 1 µg/kg to 40 mg/kg, 5 µg/kg to 30 mg/kg, or 10 µg/kg to 20 mg/kg. In one example of the present invention, GCV was administered at a daily dose of 50 mg/kg.

GCV or ACV may be administered at least once during or after the administration of the oncolytic virus. Specifically, GCV or ACV may be administered for about 2 weeks from 24 hours after the administration of the oncolytic virus. GCV or ACV may be consecutively administered twice a week for 5 to 18 days, after the administration of the oncolytic virus.

The cancer may be selected from the group consisting of lung cancer, colorectal cancer, prostate cancer, thyroid cancer, breast cancer, brain cancer, head and neck cancer, esophageal cancer, skin cancer, thymic cancer, gastric cancer, colon cancer, liver cancer, ovarian cancer, uterine cancer, bladder cancer, rectal cancer, gallbladder cancer, biliary tract cancer, pancreatic cancer, non-small cell lung cancer, bone cancer, intraocular melanoma, perianal cancer, fallopian tube carcinoma, endometrial carcinoma, cervical cancer, vaginal carcinoma, vulvar carcinoma, Hodgkin's disease, small intestine cancer, endocrine adenocarcinoma, parathyroid cancer, adrenal cancer, soft tissue sarcoma, urethral cancer, penile cancer, chronic leukemia, acute leukemia, lymphocytic lymphoma, kidney cancer, ureteral cancer, renal cell carcinoma, renal pelvis carcinoma, central nervous system tumors, primary central nervous system lymphoma, spinal cord tumor, brainstem glioma, pituitary adenoma, and a combination thereof.

The pharmaceutical composition of the present invention may further comprise a physiologically acceptable carrier. In addition, the pharmaceutical composition of the present invention may further comprise suitable excipients and diluents conventionally used in the preparation of pharmaceutical compositions. In addition, it can be formulated in the form of an injection according to a conventional method.

The pharmaceutical composition may be formulated into sterilized aqueous solutions, non-aqueous solutions, suspensions, emulsions, freeze-dried preparations, suppositories, or the like for parenteral administration. For non-aqueous solution and suspension, propylene glycol, polyethylene glycol, vegetable oil such as olive oil, injectable ester such as ethyl oleate, and the like may be used. As the suppository base, Witepsol™, macrogol, Tween™61, cacao butter, laurin fat, glycerogelatin, and the like may be used.

The pharmaceutical composition may be administered to a subject in a variety of ways and amounts depending on the condition of the patient and the presence or absence of side effects, and the optimal way, dosage, and frequency of administration may be selected by a person skilled in the art within a suitable range. In addition, the pharmaceutical composition may be administered in combination with other drug or physiologically active substance of which therapeutic effect is known to the disease to be treated, or may be formulated in combination with other drugs.

The pharmaceutical composition may be administered parenterally, including intratumoral, intraperitoneal, subcutaneous, intra-dermal, intra-nodal and intravenous administration, and the like. Preferably, it can be intra-tumor, intraperitoneal or intravenous administration. On the other hand, the dosage of the pharmaceutical composition may be determined according to the administration schedule, the dosage, and the health condition of the patient.

The term "individual" as used herein means a person who is in a condition that a disease can be relieved, suppressed or treated by the administration of the cancer cell-targeting composition of the present invention, or who is suffering from a disease.

In addition, the oncolytic virus and GCV may be administered in combination with other drug or physiologically active substance of which therapeutic effect is known to the disease to be treated, or may be formulated in the form of a combination preparation with other drugs.

A still further aspect of the present invention provides a method for preparing a recombinant vaccinia virus which expresses an HSV-TK fragment or a variant thereof, comprising the steps of: i) transfecting a shuttle plasmid comprising a nucleotide sequence encoding an HSV-TK fragment or a variant thereof into a host cell, and treating the host cell with a wild type vaccinia virus; ii) culturing the resulting host cell; and iii) obtaining the recombinant vaccinia virus from the resulting culture.

The HSV-TK fragment may be an HSV1-TK fragment. One embodiment of the HSV1-TK fragment may be any one of the fragments where 1 to 195, 24 to 149, or 30 to 46 amino acid residues from the C-terminal of the amino acid sequence represented by SEQ ID NO: 1 are consecutively deleted. Specifically, the HSV1-TK fragment may be the one where 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110, 120, 130, 140, 150, 160, 170, 180, 190, or 195 amino acid residues from the C-terminal of the amino acid sequence represented by SEQ ID NO: 1 are consecutively deleted. Preferably, the HSV1-TK fragment may be the one where 24, 30, 70, 99, 149, or 195 amino acid residues from the C-terminal of the amino acid sequence represented by SEQ ID NO: 1 are consecutively deleted. The HSV1-TK fragment may have a reduced sensitivity to GCV due to the deletion of some amino acid residues at the C-terminal.

One example of the HSV1-TK fragment may be the one where 195, 149, 99, 70, 46, 30, or 24 amino acid residues from the C-terminal of the amino acid sequence represented by SEQ ID NO: 1 are consecutively deleted. Specifically, the HSV1-TK fragment may have any one of the amino acid sequences selected from the group consisting of SEQ ID NOS: 2 to 6.

The nucleotide sequence encoding the HSV1-TK fragment may be a nucleotide sequence encoding any one of the HSV1-TK fragments where 1 to 195, 24 to 149, or 30 to 46 amino acid residues from the C-terminal of the amino acid sequence represented by SEQ ID NO: 1 are consecutively deleted. Specifically, the nucleotide sequence encoding the HSV1-TK fragment may be a nucleotide sequence encoding any one of the amino acid sequences selected from the group consisting of SEQ ID NOS: 2 to 6. Preferably, the nucleotide sequence encoding the HSV1-TK fragment may be the nucleotide sequence of SEQ ID NO: 9.

The variant of the HSV-TK fragment may be a variant of the HSV1-TK fragment. Specifically, the variant of the HSV1-TK fragment may be the one in which at least one of the amino acid residues constituting the HSV1-TK fragment is substituted. In particular, the variant of the HSV1-TK fragment may comprise $1^{st}$ to $145^{th}$ amino acid residues of the amino acid sequence of SEQ ID NO: 1. In one embodiment, the variant of the HSV1-TK fragment may have the amino acid sequence of SEQ ID NO: 7 or 8. The nucleotide sequence encoding the variant of the HSV1-TK fragment may be the nucleotide sequence of SEQ ID NO: 10 or 11.

The transfection may be carried out by various methods. Specifically, transfection methods such as $CaCl_2$ precipitation, Hanahan method of which efficiency is enhanced by using DMSO (dimethyl sulfoxide) in $CaCl_2$ precipitation, electroporation, calcium phosphate precipitation, protoplast fusion, stirring with silicon carbide fiber, *Agrobacterium*-mediated transfection, transfection using PEG, dextran sulfate, lipofectamine, and dryness/inhibition-mediated transfection may be used.

In addition, the host cell may be yeast cells such as *Saccharomyces cerevisiae* and *Schizosaccharomyces pombe* etc.; fungal cells such as *Pichia pastoris*; Insect cells such as *Drosophila* and *Spodoptera* Sf9 cells; animal cells such as CHO cells, HeLa cells, COS cells, NSO cells, 293 cells, and bow melanoma cells; or plant cells. In one embodiment, the host cell may be HeLa cells.

The wild-type vaccinia virus may be Western Reserve (WR), NYVAC (New York Vaccinia Virus), Wyeth (The New York City Board of Health; NYCBOH), LC16m8, Lister, Copenhagen, Tian Tan, USSR, TashKent, Evans, IHD-J (International Health Division-J) or IHD-W (International Health Division-White) strain, but not limited thereto.

The shuttle plasmid and the wild-type vaccinia virus may comprise a homologous region of the same vaccinia virus gene. The shuttle plasmid and the wild-type vaccinia virus may preferably comprise different replication origin and/or markers so that each element can be screened.

The host cell may be cultured using methods known in the art. Specifically, the culture method is not particularly limited as long as it can produce recombinant vaccinia virus expressing the HSV1-TK fragment of the present invention. Specifically, the culturing can be carried out continuously in a fed batch or a repeated fed batch process.

The culture medium used for culturing may be a conventional culture medium containing an appropriate carbon source, nitrogen source, amino acid, vitamin, and the like, in which needs of a particular strain can be met in an appropriate manner by adjusting the temperature, pH, etc., under aerobic conditions. As a carbon source, a mixed sugar of glucose and xylose may be used as a main carbon source. Other carbon sources may include sugars and carbohydrates such as sucrose, lactose, fructose, maltose, starch, and cellulose; oils and fats such as soybean oil, sunflower oil, castor oil, and coconut oil; fatty acids such as palmitic acid, stearic acid and linoleic acid; alcohols such as glycerol and ethanol; organic acids such as acetic acid. In addition, the carbon sources may be used alone or as a mixture. In one embodiment, the culture medium may be EMEM medium containing fetal bovine serum.

In addition, suitable precursors may be used in the culture medium. The raw materials may be added to the culture by a suitable method in a batch, fed-batch or continuous manner in the course of culturing, but not particularly limited thereto. The pH of the culture may be adjusted by using a basic compound such as sodium hydroxide, potassium hydroxide, ammonia, or an acid compound such as phosphoric acid or sulfuric acid in a suitable manner.

In addition, bubble formation can be suppressed by using a defoaming agent such as fatty acid polyglycol ester. In order to maintain aerobic conditions, oxygen or oxygen-containing gas (e.g., air) is injected into the culture. The temperature of the culture may range usually from 27° C. to 37° C., preferably from 30° C. to 35° C. The culturing time may range from 2 hours to 80 hours. Preferably, the culturing time may range from 4 hours to 76 hours.

A method for obtaining virus from the culture comprises: harvesting host cells, subjecting the cells to repeated freeze/thaw cycles to obtain a cell lysate, subjecting the cell lysate to repeated freeze/thaw cycles to obtain crude virus, repeating plaque isolation by using the crude virus to obtain pure recombinant vaccinia virus. However, the method is not limited thereto.

A still further aspect of the present invention provides a use of the oncolytic virus for treating a cancer.

A still further aspect of the present invention provides a use of the pharmaceutical composition for treating a cancer.

A still further aspect of the present invention provides a use of the oncolytic virus for the manufacture of a medicament for treating a cancer.

A still further aspect of the present invention provides a use of the pharmaceutical composition for the manufacture of a medicament for treating a cancer.

MODE FOR THE INVENTION

Hereinafter, the present invention will be described in detail with reference to examples. However, the following examples are for illustrative purposes only and are not intended to limit the scope of the invention.

Example 1. Preparation of Recombinant Vaccinia Virus (OTS-412)

Example 1.1. Construction of Shuttle Plasmid Vector

Wild-type vaccinia virus (NYC Department of Health strain, VR-1536) was purchased from the American Type Culture Collection (ATCC). For recombination, pUC57amp+ (Genewiz, USA) comprising HSV1-TK gene (pSE/L promoter) and firefly luciferase reporter gene (p7.5 promoter) was used as a shuttle plasmid vector (FIG. 1).

Example 1.2. Preparation of Recombinant Vaccinia Virus

In order to secure a recombinant virus, HeLa cells (ATCC) were prepared in a 6-well plate at a condition of $4 \times 10^5$ cells/well and in a state of EMEM medium containing 10% fetal bovine serum. Then, the cells were treated with 0.05 MOI of wild-type vaccinia virus. After 2 hours, the medium was replaced with EMEM medium containing 2% fetal bovine serum, and then the cells were transfected with 4 g of the linearized shuttle plasmid vector as constructed in Example 1.1 by employing Xfect™ polymer (Clontech 631317, USA). After incubation for 4 hours, the medium was replaced with fresh EMEM medium containing 2% fetal bovine serum, and then the cells were further incubated for 72 hours. The luciferase activity in HeLa cells was confirmed to obtain the recombinant vaccinia virus containing HSV1-TK gene.

Figure 2:
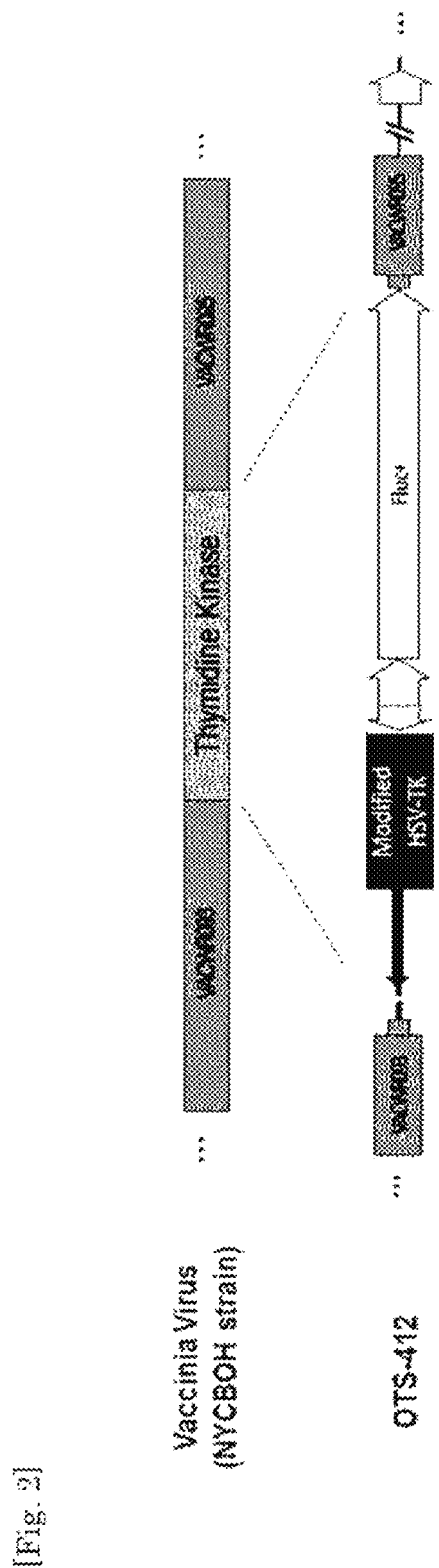
FIG. 2 is a schematic diagram showing an example of recombinant vaccinia virus, OTS-412, where the HSV1-TKmut gene and firefly luciferase gene are inserted into the TK gene region.
Figure 3:
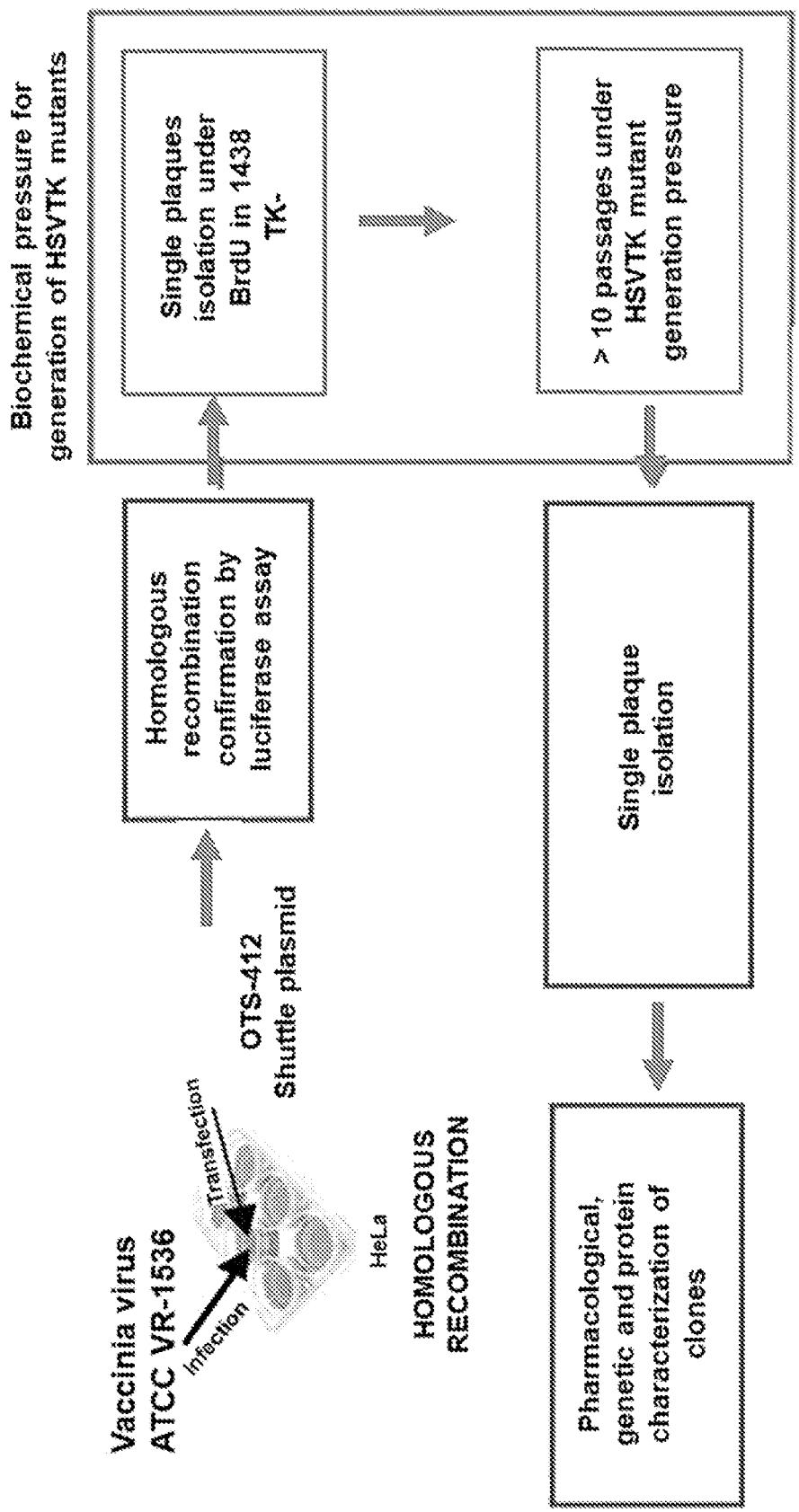
FIG. 3 illustrates a process for preparing recombinant vaccinia virus (OTS-412) expressing the HSV1-TK fragment.

Thereafter, HSV1-TK mutant was obtained from ten successive sub-cultures in a TK− osteosarcoma cell line (osteosarcoma 143 TK−), in the presence of BrdU (thymidine analogue, 15 μg/ml), under the condition of applying a biochemical environment for selecting the cells lacking TK function (TK− selection pressure). Amino acid sequencing of the mutated vaccinia virus was commissioned to Macrogen Inc. As a result, it was confirmed that, in the mutated vaccinia virus, the codon (caa) coding for glutamine (Gln) which is the $46^{th}$ amino acid of the C-terminal of HSV1-TK was point mutated with a stop codon. In addition, it was confirmed that the C-terminal amino acid residues after the $46^{th}$ one of HSV1-TK were deleted in the mutated vaccinia virus. Finally, mutated vaccinia virus OTS-412 expressing a genetically stable HSV1-TK fragment was obtained (FIGS. 2 and 3).

Further, the HSV1-TK genes of some mutants were analyzed to confirm that 24, 30, 70, 99, 149 or 195 amino acids were deleted from the C-terminal of HSV1-TK. Furthermore, analysis of the HSV1-TK genes of other mutants revealed variants of HSV1-TK fragment consisting of 181 or 227 amino acids, including the $1^{st}$ to $145^{th}$ amino acid residues from the N-terminal of HSV1-TK.

Example 2. Identification of HSV1-TK Fragment Expression in OTS-412

Figure 4:
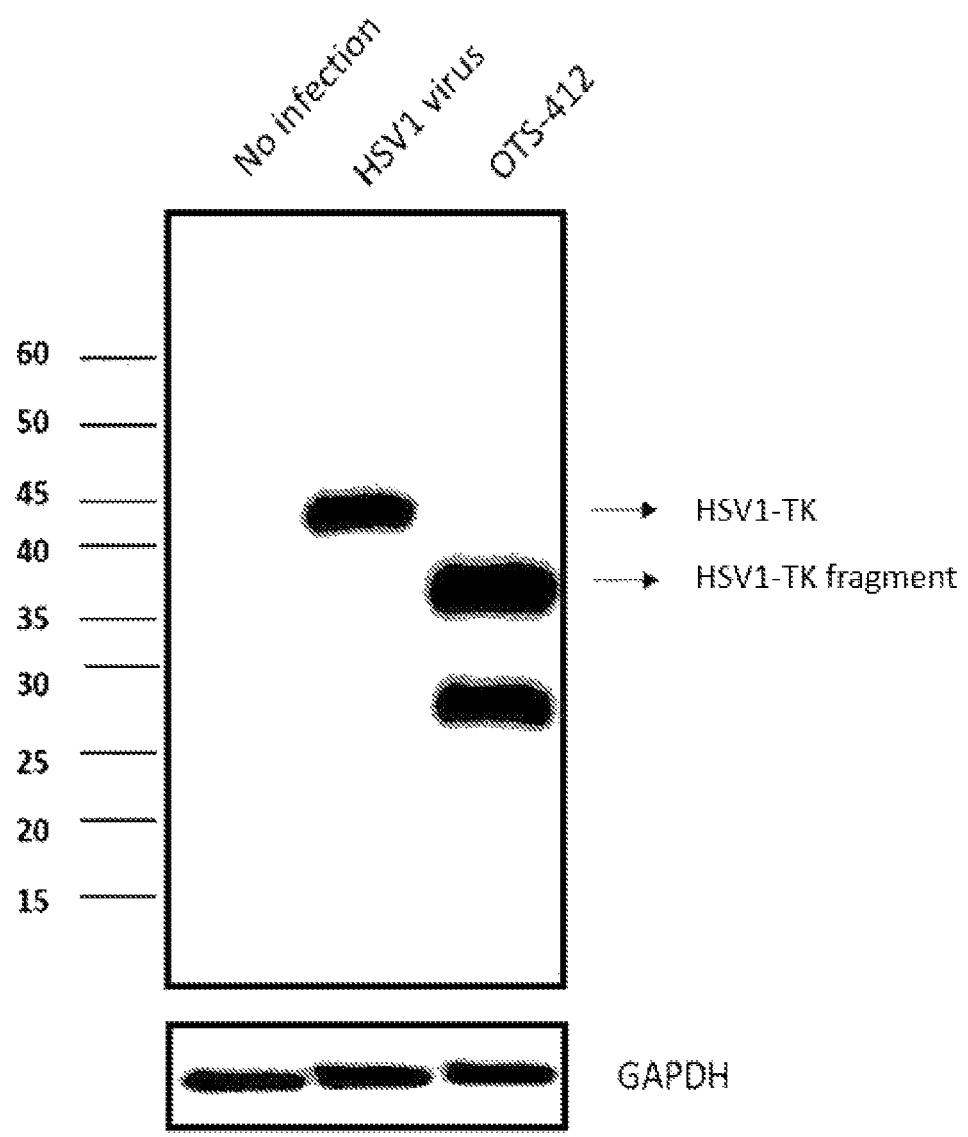
FIG. 4 depicts the result of western blotting for confirming the expression of HSV1-TK fragment in OTS-412.

To confirm that the OTS-412 prepared in Example 1.2 expresses the HSV1-TK fragment, OTS-412 was infected into HeLa cells, and the resulting cells were collected after 24 hours and lysed to extract proteins. The extracted proteins were denatured and then loaded on SDS-PAGE gels (40 μg per sample). After electrophoresis, the protein bands were transferred to the PVDF membrane and reacted with a primary antibody, anti-HSV1-TK antibody. After washing with PBST, the protein bands were reacted with a secondary antibody, HRP-labeled anti-goat antibody. After washing with PBST, the protein bands were treated with a chemiluminescent reagent and detected with a Chemiluminescent Image system (Davinch K). As a result, it was confirmed that the HSV1-TK fragment protein was expressed in the virus (FIG. 4).

Example 3. Confirmation of HSV1-TK$_{mut}$ Gene Expression in OTS-412

To confirm the introduction of the HSV1-TK$_{mut}$ gene expression in OTS-412, wild type vaccinia virus and OTS-412 were identified by restriction enzyme mapping. After respectively infecting the wild-type vaccinia virus and OTS-412 into human osteosarcoma cells, the viruses were isolated and viral genomic DNAs were extracted to obtain a negative control (Wild type-VV) and a positive control (OTS-412).

Figure 5:
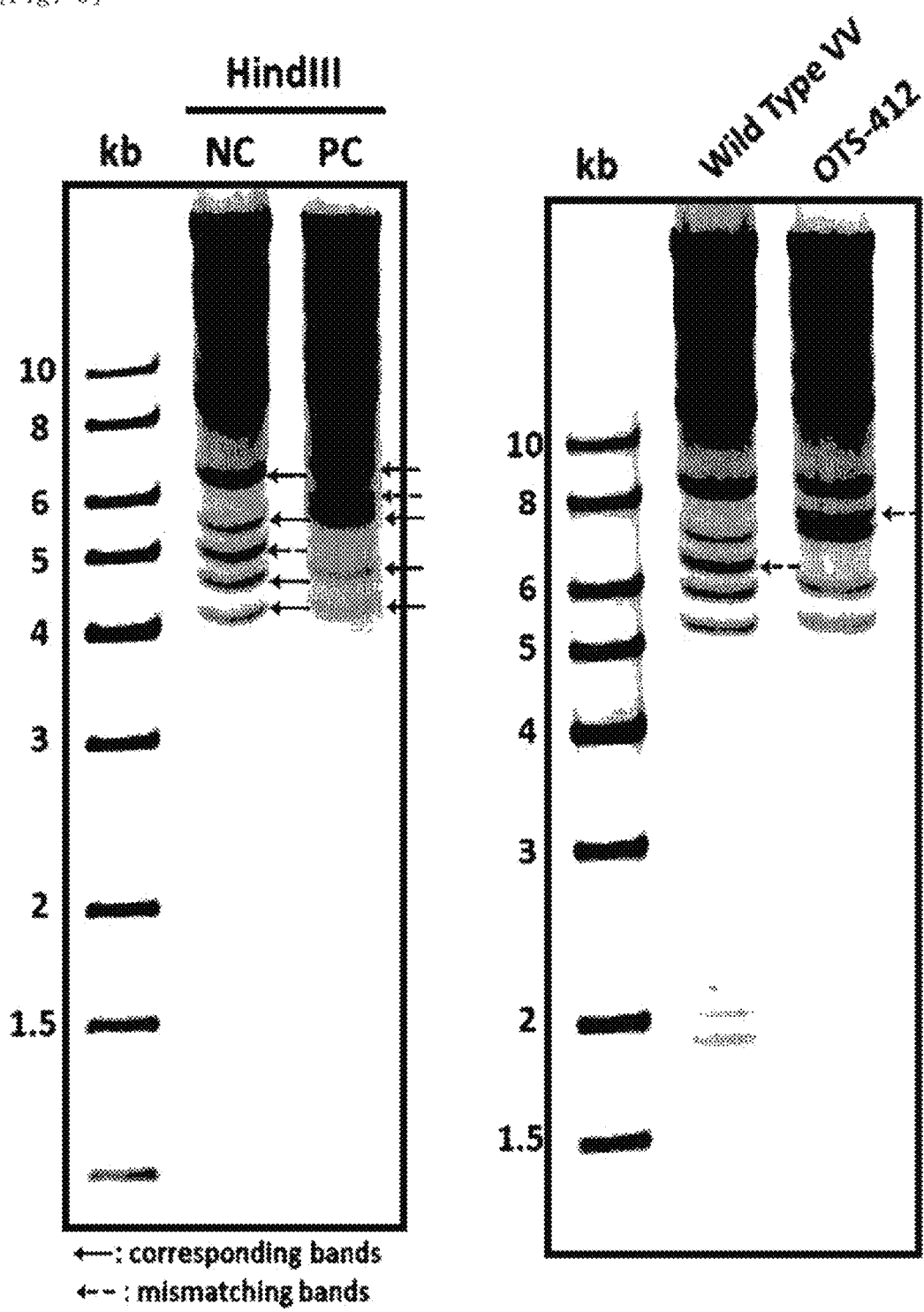
FIG. 5 indicates the result of a restriction enzyme mapping for confirming the insertion of the HSV1-TK$_{mut}$ gene in OTS-412 DNA.

The obtained viral DNAs were digested with HindIII restriction enzyme (10 units/2.5 μg) and separated by size using a DNA electrophoresis apparatus (FIG. 5). As a result, when comparing the negative control group and the positive control group, four corresponding bands (arrows) and one mismatching band (dotted arrow) between 4 kb and 8 kb were identified. The mismatching band had a large gene size, which showed that the HSV1-TK$_{mut}$ gene and the firefly luciferase gene were inserted into the TK region of vaccinia virus. It was confirmed as a unique band pattern of OTS-412 different from that of the wild-type vaccinia virus. When the wild-type vaccinia virus and OTS-412 after several passages were compared with the control groups, the same band patterns as those of the respective control groups were observed, confirming that the HSV1-TK$_{mut}$ gene in OTS-412 had genetic stability.

Example 4. Confirmation of the Reduction in Replicability of OTS-412 by GCV Administration (In Vitro)

The ability of OTS-412 prepared in Example 1.2 to infect cancer cells and proliferate was confirmed as follows. The HCT-116 cancer cell line was treated with 1 MOI (1 pfu/cell) of OTS-412, and after 24 hours and 48 hours, respectively, virus titers were measured by plaque assay.

As a result, after 24 hours, it was confirmed that the cancer cell line was infected with OTS-412. After 48 hours, it was confirmed that the viral replication was increased about 2.5 times as compared to that of 24 hours post infection (FIG. 6).

In order to confirm the effect of GCV in OTS-412 replication, Quantitative PCR analysis (qPCR) was performed based on E9L, which is specially expressed only in vaccinia virus.

Specifically, a probe that recognized E9L gene while binding to only one of two complementary DNA strands was prepared. The prepared probe allowed one luminescence to be measured when the virus replicates once. NCI-H460 and NCI-H23 cancer cells were treated with either 1 or 0.1 MOI (1 or 0.1 pfu/cell) of OTS-412 alone or in combination with GCV for 2 hours, and the resulting infected cells were cultured for 48 hours. Then, viral DNA was extracted using a viral DNA extraction kit and diluted to the concentration of 1 ng/5 μl, and then qPCR was conducted using the same.

Figure 7:
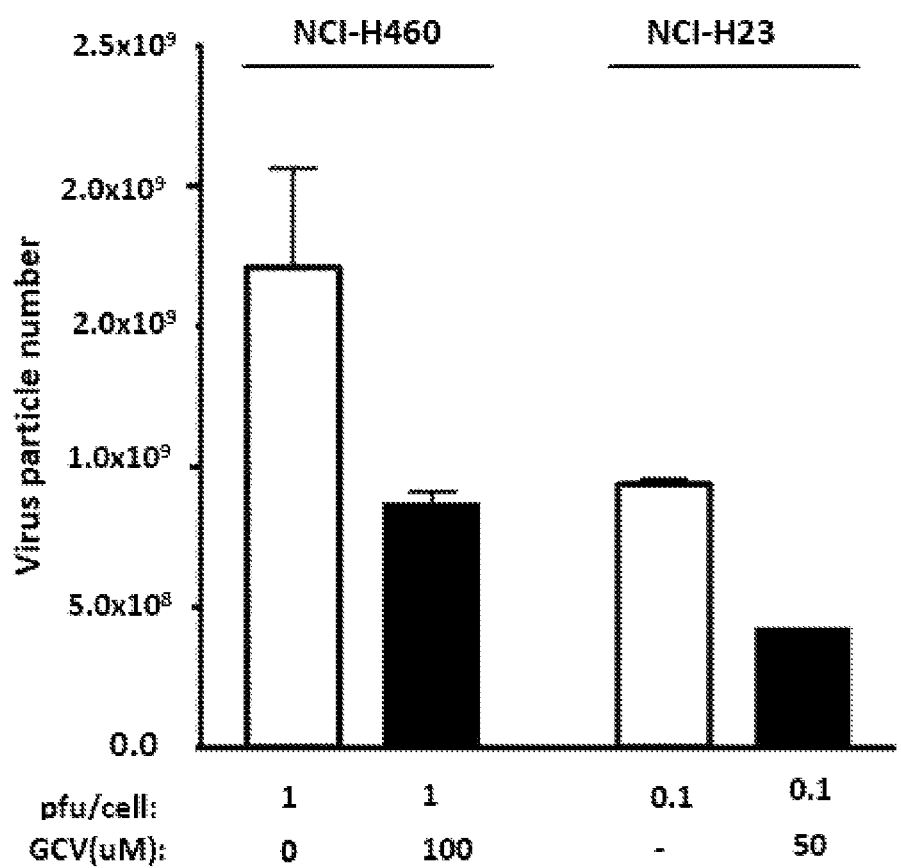
FIG. 7 is a graph showing inhibition of viral replication by GCV in OTS-412 treated NCI-H460 and NCI-H23 cancer cell lines.

As a result, it was confirmed that, in both the NCI-H460 and NCI-H23 cancer cell lines, the replication capacity of OTS-412 was reduced by about 45% when OTS-412 was administered in combination with GCV, as compared with the case where OTS-412 alone was administered (FIG. 7). This result demonstrated that the HSV1-TK fragment in OTS-412 is sensitive to GCV.

Example 5. Cytotoxicity of OTS-412 (In Vitro)

To determine whether cytotoxicity of OTS-412 was maintained despite the inhibition of OTS-412 virus replication by GCV, the cytotoxicity between the following groups was compared: groups treated with the wild type HSV1-TK-expressing vaccinia virus, alone or in combination with GCV, and groups treated with OTS-412, alone or in combination with GCV. Specifically, HCT-116 cancer cells were treated with 0.05 MOI (0.05 pfu/cell) of wild type HSV1-TK-expressing vaccinia virus or OTS-412, alone or in combination with GCV (50 μg). The resulting cells were cultured for 72 hours and analyzed for cytotoxicity using CCK8 (Cell Counting Kit 8).

Figure 8:
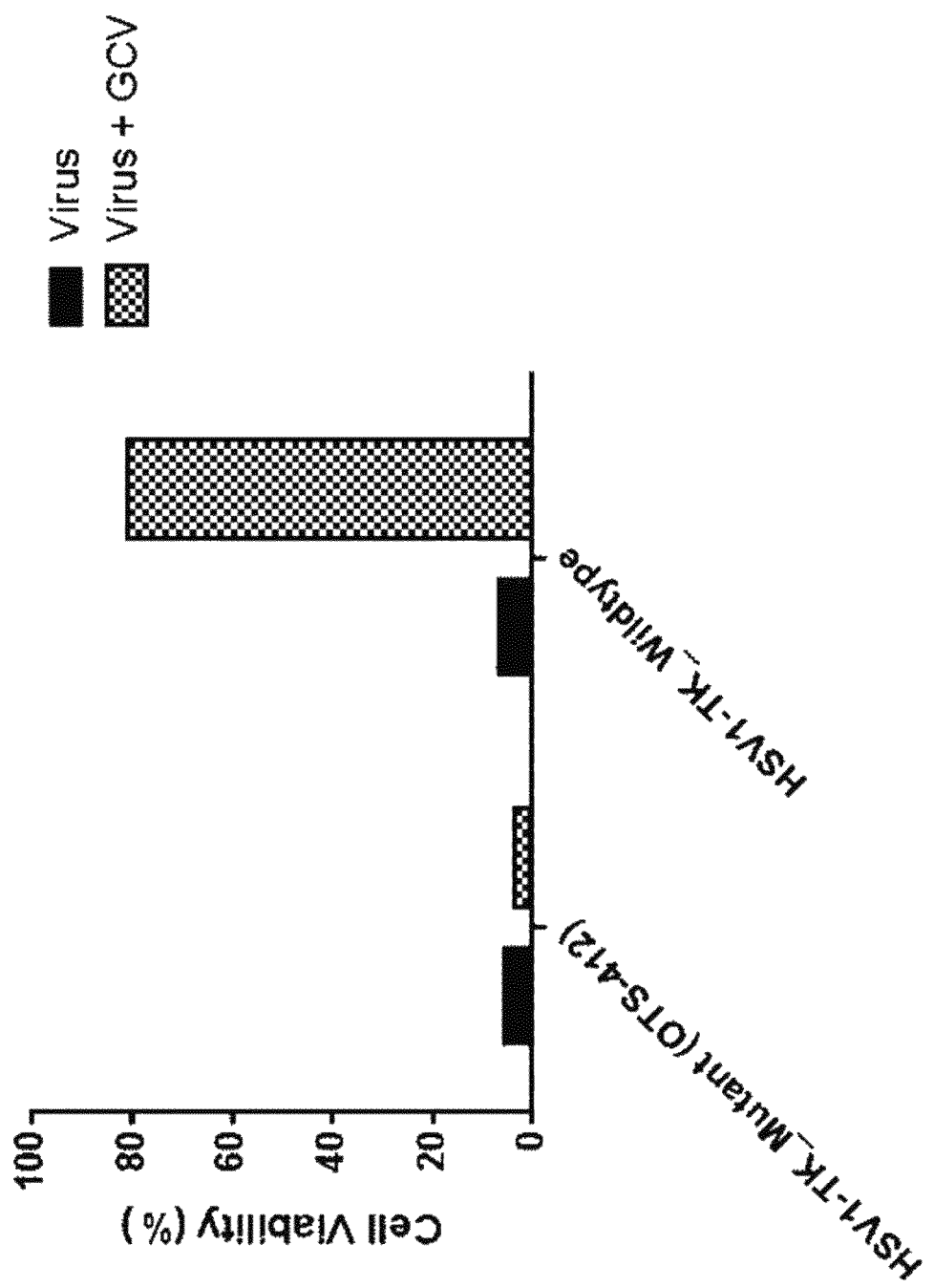
FIG. 8 is a graph showing enhancement of cytotoxicity by GCV in OTS-412 treated HCT-116 cancer cell line.

As a result, the cytotoxicity of OTS-412 and GCV combined treatment was maintained at 95% or more of OTS-412 single treated group whereas the vaccinia virus expressing wild-type HSV1-TK showed almost no cytotoxicity (FIG. 8). It was confirmed that the vaccinia virus expressing wild-type HSV1-TK had higher sensitivity to GCV than HSV1-TK$_{mut}$ inserted in OTS-412 and that the cancer cell killing effect was hardly observed due to the complete inhibition of viral replication.

Example 6. Confirmation of Anticancer Effect Upon Administration of OTS-412 in Combination with GCV (In Vitro)

In order to confirm the anticancer effect of the combined administration of OTS-412 and GCV, the cytotoxicity according to the administration of OTS-412 and GCV was evaluated in two human lung cancer cell lines, A549 and NCI-H460 cancer cell lines, and two human colorectal cancer cell lines, HT-29 and HCT-116 cancer cell lines.

Specifically, A549, NCI-H460, HT-29 and HCT-116 cancer cell lines were infected with OTS-412 at 0.01, 0.1 or 1 MOI. Three infected cancer cell lines (A549, NCI-H460, and HT-29) were treated with 100 M GCV, and the infected HCT-116 cancer cell line, with 50 M GCV. The cells were cultured for 72 hours and analyzed for cytotoxicity using CCK8 (Cell Counting Kit 8).

As a result, in NCI-H460 and HCT-116 cancer cell lines, the viability of cancer cells treated with the combination of OTS-412 and GCV was significantly lower than that of cancer cells treated with OTS-412 alone. On the other hand, in A549 and HT-29 cancer cell lines, no significant difference was observed between the viability of cancer cells treated with the combination of OTS-412 and GCV and that of the cancer cells treated with OTS-412 alone. This result demonstrates the additional cytotoxic effect by GCV as well as the direct cancer cell death by OTS-412 (FIG. 9).

In addition, the apoptosis and necrosis according to the combined administration of OTS-412 and GCV were confirmed by flow cytometry (FACS). Specifically, A549 and NCI-H460 cell lines were treated with GCV alone, OTS-412 alone, or a combination of OTS-412 and GCV, respectively, and the cells were subjected to Annexin V/PI staining followed by flow cytometry. At this time, the viability of cell was determined based on the facts that: both Annexin V and PI are negative in living cells; Annexin V is positive in the early stage of apoptosis, wherein the permeability of cell membrane changes; and both Annexin V and PI are positive at the end of apoptosis, wherein the nucleus is exposed by destruction of the cell membrane.

Figure 10:
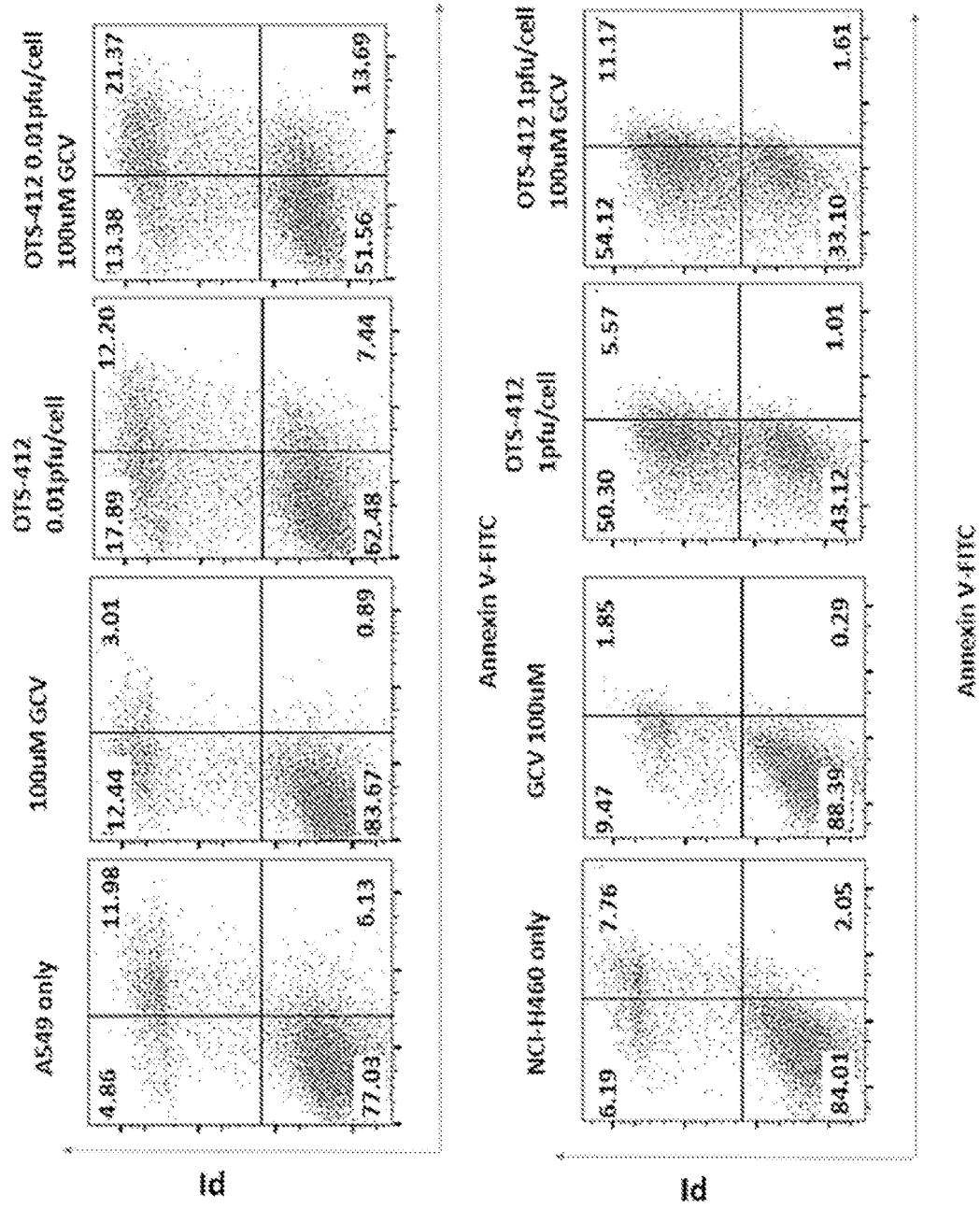
FIG. 10 demonstrates the apoptosis and necrosis patterns of A549 and NCI-H460 cancer cell lines, after administration of GCV, OTS-412, or in combination of OTS-412 and GCV, respectively.

As a result, the apoptosis by treatment with GCV alone was not confirmed. However, when A549 cells were treated with OTS-412 alone, the apoptosis rate was observed as 19.64%, and with combined treatment of OTS-412 and GCV, 35.06%. In addition, when NCI-H460 cells were treated with OTS-412 alone, the apoptosis rate was observed as 6.58%, and with combined treatment of OTS-412 and GCV, 12.78% (FIG. 10). In addition, FACS results were quantified and compared with each other. As a result, an additional toxic effect by GCV was confirmed, compared to the group treated with OTS-412 alone (FIG. 11).

Example 7. Confirmation of Anticancer Effect Upon Combined Administration of OTS-412 and GCV (In Vivo)

Example 7.1. Confirmation of the Anticancer Effect Upon Combined Administration of OTC-412 and GCV Using an HCT-116 Cancer Cell Line-Implanted Mouse Model (Intratumoral Administration)

Balb/c mice (female, 8 weeks), which were obtained from Orient Bio (Busan), were acclimated for one week and subjected to xenograft with 5×10$^6$ cells of HCT-116 human colon cancer cell line (Korean Cell Line Bank). When the tumor size reached 100 mm$^3$ to 150 mm$^3$, OTS-412 was intratumorally administered alone or in combination with GCV.

The human colon cancer cell-implanted mice thus prepared were divided into three groups. The group receiving saline in the tumor was set as a negative control and the group receiving the oncolytic virus (OTS-412, 1×10$^6$ pfu) in a intratumoral manner was set as a positive control. In addition, the group receiving the combination of the oncolytic virus (OTS-412, 1×10$^6$ pfu) and GCV (25 mg/kg) intratumorally was set as the experimental group. Each drug was administered once on day 1.

On day 12 after the administration, the tumor size of the mice in each group was measured. The tumor size of the negative control mice was measured as 600 mm$^3$, and that of the positive control mice was measured as 200 mm$^3$, which was about 66% smaller than that of the negative control mice. On the other hand, the tumor size of the experimental group mice was measured as 150 mm$^3$, which is about 75% smaller than that of the negative control mice (FIG. 12). It was confirmed that the combined administration of OTS-412 and GCV to the human colon cancer cell line increased the anticancer effect.

To confirm the virus distribution, bioluminescence image analysis was performed for each group on day 7. The mouse was fixed on OPTIX MX3 equipment and D-luciferin was injected thereto under anesthesia to obtain Bioluminescence images. Comparing the fluorescence intensities of the groups administered with OTS-412 alone or in combination with GCV, it was confirmed that the virus replication was inhibited upon combination with GCV (FIG. 13).

In order to confirm the inhibition of virus replication, tumor tissues were isolated from mice sacrificed on day 12, and genomic DNA was extracted therefrom. Quantitative PCR analysis (qPCR) was performed based on E9L, which is specifically expressed only in vaccinia virus.

As a result, when OTS-412 and GCV were administered in combination, DNA copy number of OTS-412 virus was detected to be about 50% lower than the group administered with OTS-412 alone, and statistically significant differences were also observed. Thus, it was confirmed that virus replication was inhibited by GCV (FIG. 14).

In addition, in order to confirm the safety of administrations with OTS-412 alone and with the combination of OTS-412 and GCV, the control group and the experimental group were administered with each drug, and then, the mice were weighed on the day of administration (day 0), day 3, day 6, day 9, and day 12. The weight of the mice was calculated by subtracting the tumor weight from the measured body weight.

As a result, mice in all three groups showed increased body weight, and there was little difference between the groups (FIG. 15). Thus, the safety of administering OTS-412 in combination with GCV was confirmed.

The above HCT-116-grafted mouse experiment showed that the combined administration of OTS-412 and GCV effectively controlled the viral replication, while maintaining the anti-cancer effect.

Example 7.2. Confirmation of the Anticancer Effect Upon Combined Administration of OTS-412 and GCV Using a Renca Cancer Cell Line-Implanted Mouse Model Balb/c mice (female, 7 weeks), which were obtained from Orient Bio (Busan), were acclimated for one week and subjected to allograft with $5 \times 10^7$ cells of Renca cancer cell line (Korean Cell Line Bank). when the size of tumor reached 300 mm$^3$ to 500 mm$^3$, the administration of oncolytic virus was started. Despite the fact that the viral replication in mouse cancer cell is limited, the experiment was conducted to show an anti-tumor effect of OTS-412 and GCV combination in allograft mouse model.

Mouse renal cell carcinoma cell line-implanted mice thus prepared were divided into three groups. The group receiving saline in the tumor was set as a negative control, and the group receiving once-weekly administration of oncolytic virus (OTS-412, $1 \times 10^7$ pfu) was set as a positive control. In addition, a group receiving the oncolytic virus (OTS-412, $5 \times 10^6$ pfu) twice a week with administration of GCV (25 mg/kg) was set as the experimental group. The oncolytic virus was administered intratumorally to the mouse renal cell carcinoma cell line-implanted mouse, and GCV was administered intraperitoneally. At this time, PBS and GCV were administered to the negative control group and the experimental group, respectively, on the day when no oncolytic virus was administered.

On day 24, the tumor size of the mice in each group was measured. The tumor size of the negative control mice was measured as 1,350 mm$^3$, and that of the positive control mice was measured as 1,200 mm$^3$, which is about 10% smaller than that of the negative control mice. On the other hand, the tumor size of the experimental group mice was measured as 700 mm$^3$, which is about 45% smaller than that of the negative control mice. Thus, it was confirmed that the combined administration of OTS-412 and GCV significantly increased the anticancer effect even in the cancer cell lines resistant to the oncolytic virus, compared to the administration of virus alone (FIG. 16).

Tumor tissues were isolated from the mice sacrificed on day 23 after administration of OTS-412, and genomic DNA was extracted therefrom. Quantitative PCR analysis was performed based on E9L, which is specifically expressed only in vaccinia virus.

As a result, when OTS-412 and GCV were administered in combination, OTS-412 virus particles were detected to be about 50% lower than the group administered with OTS-412 alone which was statistically significant. Thus, it was confirmed that virus replication was effectively controlled by GCV (FIG. 17).

On day 24 after administration of OTS-412, the mice were sacrificed and tumor tissues isolated therefrom were subjected to TUNEL assay. The tissues were fixed with paraformaldehyde and then sectioned. Thereafter, the sectioned tissue was subjected to antigen retrieval with Proteinase K for 15 minutes, and then treated with dUTP-labeled FITC by employing an apoptosis detection kit to observe apoptosis of tumor tissue.

As a result, it was confirmed that apoptosis was increased in the group treated with the combination of OTS-412 and GCV (FIG. 18). At this time, the dead cells were represented by red fluorescence (TRITC), and the nuclei of the cells were stained with blue fluorescence (DAPI). For the statistical processing of the images obtained in TUNEL assay, the area of apoptosis was quantified. As a result, it was confirmed that the group administered with OTS-412 in combination with GCV showed the apoptosis rate twice as high as the group administered with OTS-412 alone (FIG. 19).

Example 7.3. Confirmation of the Anticancer Effect Upon Combined Administration of OTC-412 and GCV Using an HCT-116 Cancer Cell Line-Implanted Mouse Model (Intraperitoneal Administration)

Balb/c mice (female, 8 weeks), which were obtained from Orient Bio (Busan), were acclimated for one week and subjected to xenograft with $2.5 \times 10^6$ cells of HCT-116 human colon cancer cell line (Korean Cell Line Bank). After observing until the size of tumor reached 100 mm$^3$ to 150 mm$^3$, OTS-412 was intraperitoneally administered, alone or in combination with GCV.

The human colon cancer cell-implanted mice thus prepared were divided into three groups. The group receiving saline in the tumor was set as a negative control and the group receiving the oncolytic virus (OTS-412, $1 \times 10^8$ pfu) in the tumor was set as a positive control. In addition, the group receiving the combination of the oncolytic virus (OTS-412, $1 \times 10^8$ pfu) and GCV (50 mg/kg) was set as the experimental group. At this time, all drugs administered intraperitoneally to HCT-116 implanted mice, and GCV was administered intraperitoneally. The oncolytic virus was administered twice a week, and PBS and GCV were administered to the negative control group and the experimental group, respectively, on the day when no oncolytic virus was administered.

When the size of the tumor was measured at the sacrifice of the mice on day 21, the size of the tumor was increased about 8 times in the negative control group, but the group administered with the combination of OTS-412 and GCV was about 40% smaller than that of the negative control group (FIG. 20).

In addition, immunohistochemistry (IHC) was also performed to determine the extent of viral infection in tumor tissues. Tumor tissues were isolated, processed into a paraffin block and then sectioned. Paraffin was removed from the tissue section by using xylene and ethyl alcohol. The tissue was subjected to antigen retrieval using a decloacking chamber, allowed to react sequentially with a primary antibody (vaccinia virus antibody, ab35219) and a FITC-conjugated secondary antibody, and then observed under a fluorescence microscope.

As a result, the oncolytic virus was not observed in the tumor tissue of the PBS-treated negative control group, while observed in that of the group administered with OTS-412. The oncolytic virus was also detected in the group administered with OTS-412 in combination with GCV, but less than that in the group administered with OTS-412 alone (FIGS. 21 and 22).

In addition, mouse tumor tissue was isolated and H & E staining was conducted. Specifically, the mice were sacrificed on day 21, and the tumor tissue was isolated, processed into a paraffin block and then sectioned. Paraffin was removed from the tissue section, and the tissue section was then sequentially immersed in hematoxylin and eosin, dried, mounted, and then observed using a slide scanner. The percentage of tumor necrosis was measured by H & E staining, and viable tumor size was measured by excluding necrotic portion from the size of the entire tumor. As a result, when compared with the control groups, it was confirmed that the degree of tumor necrosis of the experimental group was significantly higher than that of the negative control group (FIG. 23).

In addition, tumor tissues of all mice in each group were subjected to H & E staining, and the sizes of tumor area excluding the necrotic portions were measured. As a result, it was confirmed that the tumor tissue area of the experimental group mice administered with the combination of OTS-412 and GCV was about 40% smaller than that of the control mice (FIG. 24).

Mice were weighed on days 3, 7, 10, 14, 17, and 21 to evaluate the toxicity of the drugs. In both groups administered with virus, although the body weight was reduced on day 3 after the virus injection, it was restored to about 95% on day 7. Thereafter, the group administered with OTS-412 and GCV in combination showed weight maintenance until day 21, confirming the safety of drug administration (FIG. 25).

Example 8. Cytotoxicity of OTS-412 in Various Cancer Cell Lines (In Vitro)

To confirm the anticancer effect of OTS-412 in various cancer cell lines, the toxicity of OTS-412 was evaluated in HeLa, PC-3, DU-145, HT-29, HCT-116, A549, NCI-H23, NCI-H460, MCF-7, MDA-MB-231, 4T1, Renca, and B16F10 cancer cell lines. HeLa, A549, 4T1, and B16F10 cancer cell lines were obtained from ATCC (USA), and the remaining nine cancer cell lines were obtained from the Korean Cell Line Bank (KCLB).

Specifically, the cancer cell lines were infected with 0.5 MOI (1 pfu/cell) of OTS-412, respectively, and the cells were cultured for 48 hours and 72 hours. Thereafter, cytotoxicity was analyzed by using CCK8 (Cell Counting Kit 8).

Analysis of thirteen cancer cell lines including a cervical cancer cell line (HeLa), lung cancer cell lines (A549, NCI-H23, and HCI-H460), prostate cancer cell lines (PC-3 and DU145), rectal cancer cell lines (HT-29 and HCT-116), breast cancer cell lines (MCF-7, MDA-MB-231, and 4T1), a melanoma cell line (B16F10), and a rat renal cell carcinoma cell line (Renca) revealed that 4T1, Renca, and B16F10 cell lines showed a survival rate of 80% or more, while showing relatively high resistance. However, the remaining cancer cell lines showed a survival rate of approximately 40% or less after 72 hours, indicating that OTS-412 showed high cytotoxicity against these cells (FIG. 26).

Further, in order to measure in vitro cytotoxicity, $IC_{50}$, which is a concentration at which viability of the cancer cells is inhibited by 50%, was measured. At this time, 0.1, 0.3, 0.6, and 1.0 MOI (pfu/cell) of OTS-412 were administered to HCT-116, SK-MEL-29, and DU145 cells, respectively. Cytotoxicity was measured by using CCK-8 (Cell Counting Kit 8), according to the manufacturer's manual. As a result, the $IC_{50}$ values of OTS-412 in HCT-116, SK-MEL-29, and DU145 cells were 0.24 pfu, 0.37 pfu, and 0.08 pfu, respectively (FIG. 27).

Example 9. Confirmation of Virus Distribution after Intraperitoneal Administration of OTS-412 (In Vivo)

A high dose of OTS-412 virus ($1 \times 10^7$ pfu/mouse) was intraperitoneally administered to HCT-116 cancer cell-implanted mice, and it was confirmed whether the systemically injected virus targeted and delivered to the tumor.

It was confirmed from the result of bioluminescence image analysis that the virus targeted the tumor. It was also confirmed that, on day 7, the virus was more replicated than on day 3 and the signal was higher (FIG. 28).

The invention claimed is:

1. A recombinant oncolytic virus comprising a nucleotide sequence encoding a truncated fragment of HSV1-TK (herpes simplex virus thymidine kinase) or a variant thereof,
   wherein the HSV1-TK comprises the amino acid sequence of SEQ ID NO: 1 and the truncated fragment of HSV1-TK is any one of fragments in which 1 to 195 amino acid residues are consecutively deleted from C-terminus of SEQ ID NO: 1, and
   wherein the variant comprises the amino acid sequence of SEQ ID NO: 7 or 8.

2. The recombinant oncolytic virus of claim 1, wherein the truncated fragment of HSV1-TK is any one of fragments in which 24 to 149 amino acid residues are consecutively deleted from the C-terminal of the amino acid sequence of SEQ ID NO: 1.

3. The recombinant oncolytic virus of claim 1, wherein the truncated fragment of HSV1-TK is any one of fragments in which 30 to 46 amino acid residues are consecutively deleted from the C-terminal of the amino acid sequence of SEQ ID NO: 1.

4. The recombinant oncolytic virus of claim 1, wherein the truncated fragment of HSV1-TK is the one in which 46 amino acid residues are consecutively deleted from the C-terminal of the amino acid sequence of SEQ ID NO: 1.

5. The recombinant oncolytic virus of claim 1, wherein the truncated fragment of HSV1-TK fragment comprises any one of the amino acid sequence selected from the group consisting of SEQ ID NOS: 2 to 6.

6. The recombinant oncolytic virus of claim 1, which is derived from adenovirus, measles virus, herpes simplex virus, lentivirus, retrovirus, cytomegalovirus, baculovirus, reovirus, adeno-associated virus, myxoma virus, vesicular stomatitis virus, poliovirus, Newcastle disease virus, parvovirus, coxsackie virus, senecavirus, vaccinia virus, or poxvirus.

7. The recombinant oncolytic virus of claim 1, which is derived from vaccinia virus.

8. A pharmaceutical composition, which comprises the recombinant oncolytic virus of claim 1 as an active ingredient and a pharmaceutically acceptable carrier.

9. The pharmaceutical composition of claim 8, which comprises the recombinant oncolytic virus in an amount of $1\times10^3$ pfu to $1\times10^{10}$ pfu/dose.

10. A pharmaceutical composition which comprises the recombinant oncolytic virus of claim 1 and GCV (ganciclovir) or ACV (acyclovir) as active ingredients and a pharmaceutically acceptable carrier.

11. The pharmaceutical composition of claim 10, which comprises the recombinant oncolytic virus in an amount of $1\times10^3$ pfu to $1\times10^{10}$ pfu/dose.

12. The pharmaceutical composition of claim 10, which comprises the GCV or ACV in an amount of 0.1 μg/kg/day to 50 mg/kg/day.

13. A method for preparing a recombinant oncolytic virus which expresses a truncated fragment of HSV1-TK (herpes simplex virus thymidine kinase) or a variant thereof according to claim 1, comprising the steps of:
   i) transfecting a shuttle plasmid comprising a nucleotide sequence encoding the truncated fragment of HSV1-TK or a variant thereof into a host cell, and treating the host cell with a wild type vaccinia oncolytic virus;
   ii) culturing the resulting host cell; and
   iii) obtaining the recombinant oncolytic virus from the resulting culture,
   wherein the oncolytic virus is a vaccinia virus,
   wherein the HSV1-TK comprises the amino acid sequence of SEQ ID NO: 1 and the truncated fragment of HSV1-TK is any one of fragments in which 1 to 195 amino acid residues are consecutively deleted from C-terminus of SEQ ID NO: 1, and
   wherein the variant comprises the amino acid sequence of SEQ ID NO: 7 or 8.

14. The method of claim 13, wherein the truncated fragment of HSV1-TK comprises any one of the amino acid sequence selected from the group consisting of SEQ ID NOs: 2 to 6.

15. The method of claim 13, wherein the nucleotide sequence encoding the truncated fragment of HSV1-TK is the nucleotide sequence of SEQ ID NO: 9.

16. The method of claim 13, wherein the nucleotide sequence encoding the variant of the truncated fragment of HSV1-TK is the nucleotide sequence of SEQ ID NOs: 10 or 11.

* * * * *